USO10201278B2

(12) United States Patent
Lux et al.

(10) Patent No.: US 10,201,278 B2
(45) Date of Patent: Feb. 12, 2019

(54) LIFE DETECTING RADARS

(71) Applicant: California Institute of Technology, Pasadena, CA (US)

(72) Inventors: James Paul Lux, Thousand Oaks, CA (US); Vaughn P. Cable, Woodland Hills, CA (US); Salman-ul Mohammed Haque, Los Angeles, CA (US); Michael Ray McKee, Lancaster, CA (US); Hirad Ghaemi, Pasadena, CA (US); Richard Kalantar Ohanian, Glendale, CA (US)

(73) Assignee: California Institute of Technology, Pasadena, CA (US)

( * ) Notice: Subject to any disclaimer, the term of this patent is extended or adjusted under 35 U.S.C. 154(b) by 315 days.

(21) Appl. No.: 14/256,748

(22) Filed: Apr. 18, 2014

(65) Prior Publication Data
US 2014/0316261 A1    Oct. 23, 2014

Related U.S. Application Data

(60) Provisional application No. 61/813,507, filed on Apr. 18, 2013.

(51) Int. Cl.
*A61B 5/00* (2006.01)
*A61B 5/024* (2006.01)
(Continued)

(52) U.S. Cl.
CPC .......... *A61B 5/0022* (2013.01); *A61B 5/024* (2013.01); *A61B 5/0507* (2013.01);
(Continued)

(58) Field of Classification Search
CPC combination set(s) only.
See application file for complete search history.

(56) References Cited

U.S. PATENT DOCUMENTS

| 3,670,327 A | 6/1972 | Clare et al. |
| 4,434,424 A | 2/1984 | Old |

(Continued)

FOREIGN PATENT DOCUMENTS

| JP | 09044779 A | 2/1997 |
| JP | 09304525 A | 11/1997 |

(Continued)

OTHER PUBLICATIONS

Chen, Kun-Mu et al., "Microwave Life-Detection Systems for Searching Human Subjects Under Earthquake Rubble or Behind Barrier", IEEE Transactions on Biomedical Engineering, Jan. 2000, vol. 27, No. 1, pp. 105-114.

(Continued)

*Primary Examiner* — Serkan Akar
*Assistant Examiner* — Farshad Negarestan
(74) *Attorney, Agent, or Firm* — KPPB LLP

(57) ABSTRACT

Systems and methods for detecting biometrics using a life detecting radar are disclosed. Life detecting radars can include transmit antennas configured to transmit continuous microwave ("CW") radio signals that reflect back upon making contact with various objects. The signal can be systematically varied in frequency to provide a signal that is essentially continuous with short gaps between transmissions at different frequencies. The reflected return signals are received by one or more receive antennas and processed to detect one or more targets. The received signal can include a static (i.e. constant phase) signal corresponding to reflections from objects that do not move. The received signal can also include a phase varying signal that corresponds to reflections from a living target having measurable biometrics including (but not limited to) breathing patterns and heartbeats. Clutter can be removed and the remaining portions of the received signal are analyzed for target detection.

19 Claims, 25 Drawing Sheets

(51) Int. Cl.

| | | |
|---|---|---|
| *A61B 5/08* | (2006.01) | |
| *A61B 5/117* | (2016.01) | |
| *A61B 5/05* | (2006.01) | |
| *A61B 5/11* | (2006.01) | |
| *G01S 7/00* | (2006.01) | |
| *G01S 13/34* | (2006.01) | |
| *G01S 13/56* | (2006.01) | |
| *G01S 13/88* | (2006.01) | |
| *G06F 19/00* | (2018.01) | |
| *G16H 40/67* | (2018.01) | |
| *A62B 33/00* | (2006.01) | |

(52) U.S. Cl.
CPC .......... *A61B 5/0816* (2013.01); *A61B 5/1126* (2013.01); *G01S 7/003* (2013.01); *G01S 13/347* (2013.01); *G01S 13/56* (2013.01); *G01S 13/88* (2013.01); *G06F 19/00* (2013.01); *G16H 40/67* (2018.01); *A61B 5/117* (2013.01); *A61B 5/7257* (2013.01); *A62B 33/00* (2013.01)

(56) References Cited

U.S. PATENT DOCUMENTS

| | | |
|---|---|---|
| 4,958,638 A | 9/1990 | Sharpe et al. |
| 4,970,519 A | 11/1990 | Minnis et al. |
| 4,991,165 A | 2/1991 | Cronyn |
| 5,086,302 A * | 2/1992 | Miller ............... H01Q 3/267 342/173 |
| 5,448,501 A | 9/1995 | Hablov et al. |
| 5,507,291 A | 4/1996 | Stirbl et al. |
| 5,760,687 A | 6/1998 | Cousy et al. |
| 5,861,021 A | 1/1999 | Thome et al. |
| 5,904,709 A | 5/1999 | Arndt et al. |
| 6,026,173 A | 2/2000 | Svenson et al. |
| 6,031,482 A | 2/2000 | Poussieres et al. |
| 6,057,761 A | 5/2000 | Yukl et al. |
| 6,208,286 B1 | 3/2001 | Rostislavovich et al. |
| 6,307,475 B1 | 10/2001 | Kelley et al. |
| 6,313,743 B1 | 11/2001 | Abraham-Fuchs et al. |
| 6,909,397 B1 | 6/2005 | Greneker, III et al. |
| 6,927,691 B2 | 8/2005 | Yukl et al. |
| 7,135,980 B2 | 11/2006 | Moore et al. |
| 7,199,749 B2 | 4/2007 | Greneker, III et al. |
| 7,646,830 B1 | 1/2010 | Weill |
| 7,679,545 B2 | 3/2010 | Rausch et al. |
| 7,889,053 B2 * | 2/2011 | McGrath ............ G07C 9/00158 340/5.1 |
| 8,378,879 B2 | 2/2013 | Lewis et al. |
| 8,721,554 B2 | 5/2014 | Lin et al. |
| 9,986,934 B2 | 6/2018 | Lux et al. |
| 2002/0138768 A1 | 9/2002 | Maurakami |
| 2003/0081503 A1 * | 5/2003 | Barnard ................ G01S 3/8086 367/103 |
| 2003/0130697 A1 | 7/2003 | Halperin et al. |
| 2003/0135097 A1 | 7/2003 | Wiederhold et al. |
| 2003/0178034 A1 | 9/2003 | Yuki et al. |
| 2004/0123667 A1 | 7/2004 | McGrath et al. |
| 2004/0243299 A1 * | 12/2004 | Scaer ...................... G08G 1/202 701/522 |
| 2005/0128124 A1 | 6/2005 | Greneker et al. |
| 2006/0028369 A1 | 2/2006 | Rausch et al. |
| 2006/0028389 A1 | 2/2006 | Yukl et al. |
| 2006/0224046 A1 * | 10/2006 | Ramadas ............. A61B 5/0002 600/300 |
| 2007/0066904 A1 | 3/2007 | Wiesmann et al. |
| 2008/0007445 A1 | 1/2008 | Leach et al. |
| 2008/0045832 A1 | 2/2008 | McGrath et al. |
| 2008/0074307 A1 | 3/2008 | Boric-Lubecke et al. |
| 2009/0146869 A1 | 6/2009 | Dwelly et al. |
| 2009/0278728 A1 * | 11/2009 | Morgan ............... A61B 5/0205 342/115 |
| 2010/0079347 A1 * | 4/2010 | Hayes .................... H01Q 1/246 343/705 |
| 2010/0109938 A1 | 5/2010 | Oswald et al. |
| 2010/0249633 A1 | 9/2010 | Droitcour et al. |
| 2010/0295718 A1 | 11/2010 | Mohamadi et al. |
| 2010/0321229 A1 | 12/2010 | Dwelly et al. |
| 2013/0002434 A1 | 1/2013 | Cuddihy et al. |
| 2015/0208945 A1 | 7/2015 | Lux et al. |
| 2015/0223701 A1 | 8/2015 | Ghaemi et al. |

FOREIGN PATENT DOCUMENTS

| | | |
|---|---|---|
| KR | 20030070315 A | 8/2003 |
| WO | 2007118274 A1 | 10/2007 |
| WO | 2008001092 A2 | 1/2008 |
| WO | 2008054490 A2 | 5/2008 |
| WO | 2008054490 A3 | 7/2008 |
| WO | 2011075639 A1 | 6/2011 |
| WO | 2012055148 A1 | 5/2012 |
| WO | 2012158840 A1 | 11/2012 |
| WO | 2014172668 A1 | 10/2014 |

OTHER PUBLICATIONS

Ghaemi, "Synthetic Aperture Weather Radar", Thesis, 2008, 78 pgs.
Hirsch et al., "Respiratory sinus arrhythmia in humans: how breathing pattern modulates heart rate", American Physiological Society, 1981, pp. H620-H629.
Li et al., "Efficient Mixed-Spectrum Estimation with Applications to Target Feature Extraction", IEEE Transactions on Signal Processing, vol. 44, No. 2, Feb. 1996, 281-295.
Liu et al., "Feature extraction of SAR targets consisting of trihedral and dihedral corner reflectors", IEE Proc.-Radar, Sonar Navig., Jun. 1998, Vo. 145, No. 3, pp. 161-172.
International Search Report and Written Opinion for International Application PCT/US2014/034700, report completed Sep. 3, 2014, dated Sep. 3, 2014, 7 Pgs.
International Preliminary Report on Patentability for International Application PCT/US2014/034700, Report issued Oct. 20, 2015, dated Oct. 29, 2015, 5 Pgs.
Extended European Search Report for European Application No. 14785477.2, Search completed Dec. 22, 2016, dated Jan. 9, 2017, 10 Pgs.
International Preliminary Report on Patentability for International Application PCT/US2007/008340, Report dated Oct. 8, 2008, 4 Pgs.
International Search Report and Written Opinion for International Application PCT/US2010/062036, report completed Aug. 31, 2011, dated Aug. 31, 2011, 6 Pgs.
"Autoregressive model", Wikipedia, Dec. 8, 2013, retrieved from https://web.archive.org/web/20150106061833/https://en.wikipedia.org/wiki/Autoregressive_model on Jul. 26, 2017, 9 pages.
"Camero—Step into the known", Camero—Tactical Through-Wall Imaging Solutions, Mar. 28, 2013, retrieved from https://web.archive.org/web/20130328000753/http://www.camero-tech.com/ on Jul. 26, 2017, 1 page.
"EMMDAR (Electro-Magnetic Motion Detection and Ranging)", L3 Communications CyTerra, 2011, retrieved from http://www.cyterra.com/products/emmdar.htm on Jul. 26, 2017.
"Tianying-Night Vision", Yiwu TianYing Optical Instrument Co., Limited, Mar. 20, 2013, retrieved from https://web.archive.org/web/20130320184606/http://www.nightvisioncn.com:80/sdp/625512/4/main-3235899/0/Home.html on Jul. 26, 2017, 2 pages.
"Least squares", Wikipedia, Jan. 30, 2014, https://web.archive.org/web/20140209133957/https://en.wikipedia.org/wiki/Least_squares on Jul. 26, 2017, 9 pages.
"TiaLinx, Inc.", TiaLinx, Inc., Jul. 15, 2012, retrieved from https://web.archive.org/web/20120715031226/www.tialinx.com/eaglefamily.html on Jul. 26, 2017, 4 pages.
Chongyu et al., "The design of cancellation unit against radiofrequency interference in life-detection radar", 2010 International Conference on Microwave and Millimeter Wave Technology, May 2010, pp. 1758-1761.
Donelli, M., "A Rescue Radar System for the Detection of Victims Trapped Under Rubble Based on the Independent Component

(56) References Cited

OTHER PUBLICATIONS

Analysis Algorithm", Progress in Electromagnetics Research M, vol. 19, Jul. 29, 2011, pp. 173-181.

Izadi et al., "Design and Simulation of a Life Detection System Based on Detection of the Heart Beat Using Doppler Frequency", 2006 IEEE International Symposium on Signal Processing and Information Technology, Aug. 27-30, 2006, Vancouver, BC, Canada, pp. 685-690.

Jianqi et al., "A New Method for Identifying the Life Parameters via Radar", EURASIP Journal on Advances in Signal Processing, vol. 2007, Article ID 31415, Jan. 30, 2007, 8 pages, doi:10.1155/2007/31415.

Liu et al., "The Application of the Hilbert-Huang Transform in Through-wall Life Detection with UWB Impulse Radar", Piers Online, vol. 6, No. 7, Jan. 2010, pp. 695-699.

Pieraccini et al., "Detection of Breathing and Heartbeat Through Snow Using a Microwave Transceiver", IEEE Geoscience and Remote Sensing Letters, vol. 5, No. 1, Jan. 2008, pp. 57-59.

Xu et al., "A Novel Method for Automatic Detection of Trapped Victims by Ultrawideband Radar", IEEE Transactions on Geoscience and Remote Sensing, vol. 50, Issue 8, Aug. 2012, pp. 3132-3142.

Zade et al., "A Modern Microwave Life Detection System for Human Being Buried Under Rubble", International Journal of Advanced Engineering Research and Studies, E-ISSN2249-8974, vol. 1, Issue 1, Oct.-Dec. 2011, pp. 69-77.

"Arduino HomePage", Arduino, Feb. 1, 2014, https://web.archive.org/web/20140201142732/https://www.arduino.cc/, 3 pages.

"Fieldnames", MathWorks, Nov. 28, 2013, https://web.archive.org/web/20131128081202/http://www.mathworks.com/help/matlab/ref/fieldnames.html, 2 pages.

"Str2num", MathWorks, Jul. 17, 2013, retrieved from https://web.archive.org/web/20130717105438/http://www.mathworks.com/help/matlab/ref/str2num.html, 2 pages.

"Teensy USB Development Board", PJRC Store, Feb. 9, 2014, retrieved from https://web.archive.org/web/20140209222648/www.pjrc.com/store/teensy3.html, 1 page.

"Teensyduino", PJRC, Feb. 9, 2014, https://web.archive.org/web/20140209215538/https://www.pjrc.com/teensy/teensyduino.html, 3 pages.

"Textscan", MathWorks, Dec. 19, 2013, retrieved from https://web.archive.org/web/20131219081941/http://www.mathworks.com/help/matlab/ref/textscan.html, 3 pages.

"Troubleshooting Common Problems", PJRC, Feb. 9, 2014, https://web.archive.org/web/20140209214600/https://www.pjrc.com/teensy/troubleshoot.html, 5 page.

* cited by examiner

LIFE DETECTING RADARS

CROSS-REFERENCE TO RELATED APPLICATIONS

The current application claims priority to U.S. Provisional Patent Application No. 61/813,507 filed Apr. 18, 2013, the disclosure of which is incorporated herein by reference.

FEDERAL FUNDING SUPPORT

This invention was made with government support under grant nos. NAS7-03001 and NNN12AA01C awarded by the National Aeronautics and Space Administration. The government has certain rights in the invention.

FIELD OF THE INVENTION

The present invention generally relates to radars and more specifically to systems and methods for detecting biometrics using radars.

BACKGROUND

Biometrics refer to the quantifiable data (or metrics) related to human characteristics and traits. The quantifiable metrics can be gathered using various sensors and the collected data processed to identify individual persons. Typically, biometric identifiers can be categorized as physiological and/or behavioral characteristics. Generally, physiological characteristics are related to the shape of the body and can include (but not limited to) fingerprint, palm print, DNA, and scent. In contrast, behavioral characteristics relate to a pattern of behavior and include (but not limited to) gait, voice, and typing rhythm. Biometric identifiers can also include characteristics that are more subtle such as breathing patterns and heart rates.

SUMMARY OF THE INVENTION

Systems and methods in accordance with embodiments of the invention use radar to detect the location of living people. One embodiment includes: at least one transmit antenna configured to propagate at least one beam using a continuous wave transmit signal set at a plurality of frequencies, where the at least one beam illuminates at least one sensing area; at least one receive antenna configured to receive a return signal associated with reflections from objects of the at least one transmit signal within the at least one sensing area, where the return signal includes at least one signal component having static phase associated with reflections from nonmoving objects and at least one signal component having time varying phase associated with at least one target; a processor; a memory containing a radar application. In addition, the radar application configures the processor to: receive the return signal from the at least one receive antenna; determine a static phase component of the return signal; generate a cancellation signal by sampling the at least one transmit signal and modulating the sampled signal such that the phase and amplitude of the cancellation signal is adjusted to match an estimated phase and amplitude of the static phase component of the return signal; process the return signal by subtracting the cancellation signal to attenuate the at least one signal component having static phase; and detect the at least one target by analyzing the at least one signal component having time varying phase for a biometric identifier by: transforming the processed return signal from a frequency to a time domain data set; generating range bins, where each range bin has a sequence of samples taken from the time domain data set; analyzing each range bin for unique targets by examining a band limited version of the processed return signal for repetitive characteristics; and matching the repetitive characteristics to a biometric identifier of a human.

In a further embodiment, the radar application further configures the processor to generate a user interface that allows the processor to receive inputs for controlling the life detecting radar.

In another embodiment, the user interface is generated on a separate device configured to communicate with the life detecting radar via a wireless communication channel.

In a still further embodiment, the life detecting radar further includes a plurality of transmit antennas configured to propagate a plurality of beams using continuous microwave limited stepped frequencies for obtaining range measurements.

In still another embodiment, the plurality of beams and frequencies rapidly switch to allow for multiple measurements to be made during a short enough time period such that the at least one target's heartbeat signal is assumed constant during the time period.

In a yet further embodiment, the plurality of beams and frequencies rapidly switch to allow for multiple measurements to be made during a short enough time period such that the at least one target's respiration signal is relatively constant.

In yet another embodiment, the biometric identifier includes at least one microwave cardiogram that can be utilized to discriminate among targets.

In a further embodiment again, the biometric identifier includes at least one breathing pattern that can be utilized to discriminate among targets.

In another embodiment again, the radar application further configures the processor to receive the return signal from the at least one receive antenna and collect samples for each sensing area at a sampling rate between 300-500 Hz.

In a further additional embodiment, the life detecting radar utilizes a plurality of radio frequency modules and an antenna switching matrix to make multiple measurements at the same time, where switching and frequency patterns are selected to prevent the same frequency from being used on two separate beams at the same period in time.

In another additional embodiment, the life detecting radar further includes a camera for collecting digital image data.

In a still yet further embodiment, the life detecting radar further includes a Global Positioning System for providing location information.

In still yet another embodiment, transforming the processed return signal from a frequency to a time domain data set includes utilizing an Inverse Fast Fourier Transform.

In a still further embodiment again, the prototype waveform is compared against a data collection of human and animal waveforms to detect the at least one target.

In still another embodiment again, a potential victim list is generated upon detecting the at least one target.

In a still further additional embodiment, detecting a target by analyzing the at least signal component further includes first identifying which targets are likely to be in the search area in front of the transmit antenna.

In still another additional embodiment, the at least one transmit antenna is further configured to propagate eight beams arranged in cardinal and intermediate directions.

In a yet further embodiment again, the at least one transmit antenna is further configured to utilize 10 frequencies.

In yet another embodiment again, the sequence of samples taken from the time domain data set includes phase and quadrature data samples.

In a yet further additional embodiment, at least one antenna is used as both a transmit antenna and a receive antenna.

An embodiment of the method of the invention includes: propagating at least one beam using a continuous wave transmit signal set at a plurality of frequencies, where the at least one beam illuminates at least one sensing area using at least one transmit antenna; receiving a return signal associated with reflections of the at least one transmit signal from objects within the at least one sensing area using at least one receive antenna, where the return signal includes at least one signal component having static phase associated with reflections from nonmoving objects and at least one signal component having time varying phase associated with at least one target; receiving the return signal from the at least one receive antenna using a life detecting radar system; determining a static phase component of the return using the life detecting radar system; generating a cancellation signal by sampling the at least one transmit signal and modulating the sampled signal such that the phase and amplitude of the cancellation signal is adjusted to match an estimated phase and amplitude of the static phase component of the return signal using the life detecting radar system; processing the return signal by subtracting the cancellation signal to attenuate the at least one signal component having static phase using the life detecting radar system; and detecting the at least one target by analyzing the at least one signal component having time varying phase for a biometric identifier by using the life detecting radar system by: transforming the processed return signal from a frequency to a time domain data set; generating range bins, where each range bin has a sequence of samples taken from the time domain data set; analyzing each range bin for unique targets by examining a band limited version of the processed return signal for repetitive characteristics; and matching the repetitive characteristics to a biometric identifier of a human.

A still further embodiment includes at least one transmit antenna configured to propagate eight beams using continuous wave transmit signals set using ten frequencies, where: the eight beams are arranged in cardinal and intermediate directions and illuminate a plurality of sensing areas to resolve a twenty meter search range; and the eight beams and ten frequencies rapidly switch to allow for multiple measurements to be made during a short enough time period such that a target's biometric identifiers are relatively constant; at least one receive antenna configured to receive a return signal associated with reflections from objects within the at least one sensing area of the at least one transmit signal, where the return signal includes at least one signal component having static phase associated with reflections from nonmoving objects and at least one signal component having time varying phase associated with at least one target; a processor; and a memory containing a radar application. In addition, the radar application configures the processor to: receive the return signal from the at least one receive antenna and collect samples for each sensing area at a sampling rate between 300-500 Hz; determine a static phase component of the return signal; generate a cancellation signal by sampling the at least one transmit signal and modulating the sampled signal such that the phase and amplitude of the cancellation signal is adjusted to match an estimated phase and amplitude of the static phase component of the return signal; process the return signal by subtracting the cancellation signal to attenuate the at least one signal component having static phase; and detect the at least one target by analyzing the at least one signal component having time varying phase for a biometric identifier by: transforming the processed return signal from a frequency to a time domain data set; generating range bins, where each range bin has a sequence of samples taken from the time domain data set; analyzing each range bin for unique targets by examining a band limited version of the processed return signal for repetitive characteristics; and matching the repetitive characteristics to a biometric identifier of a human.

DETAILED DESCRIPTION OF THE DRAWINGS

Figure 1:
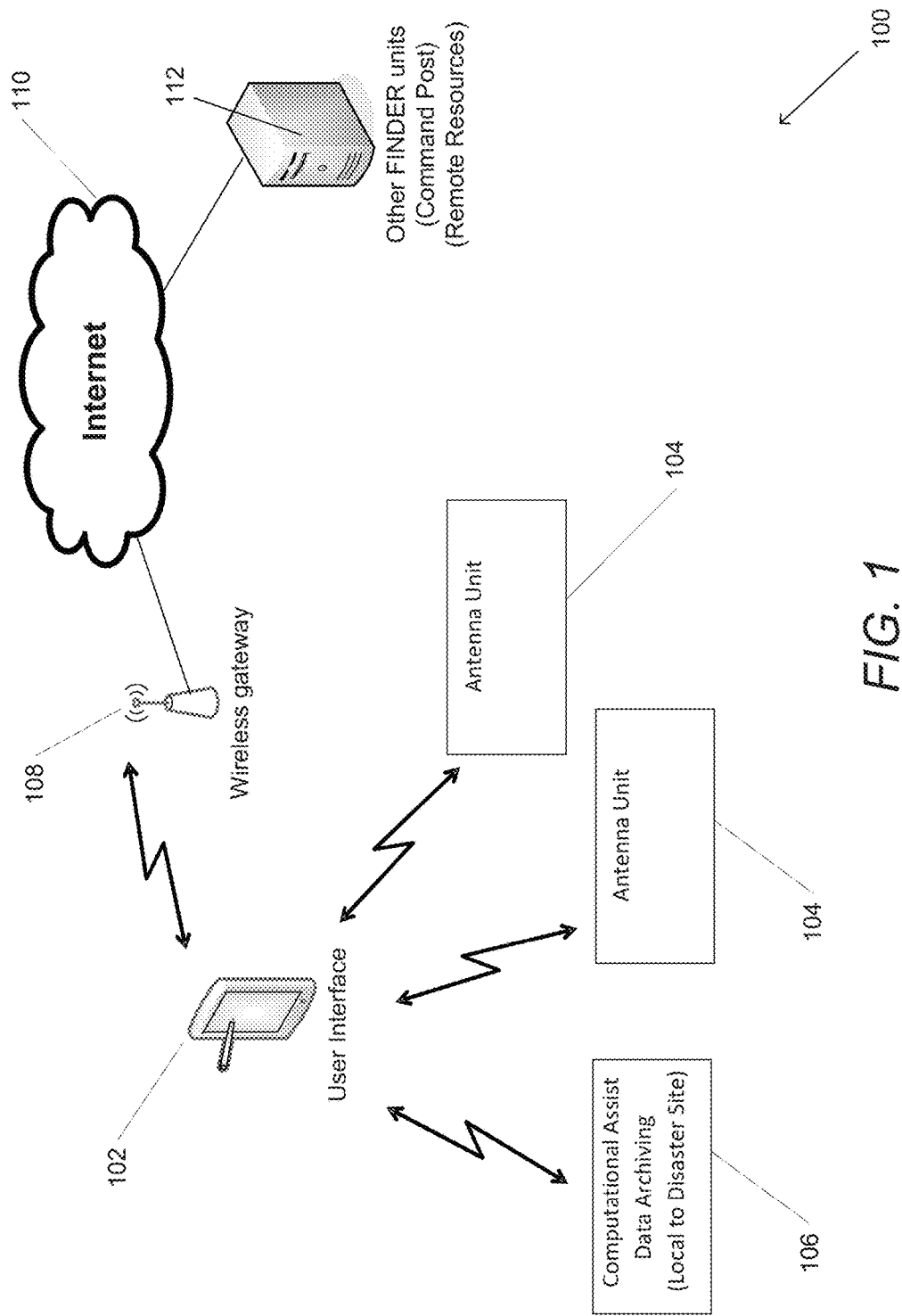
FIG. 1 is a system diagram of a life detecting radar ("FINDER") in accordance with an embodiment of the invention.

Turning now to the drawings, systems and methods for detecting biometrics using a life detecting radar in accordance with embodiments of the invention are disclosed. In many embodiments, life detecting radars include one or more transmit antennas configured to transmit continuous microwave ("CW") radio signals that reflect back upon making contact with various objects. In many embodiments, the signal is systematically varied in frequency to provide a signal that is essentially continuous with short gaps between transmissions at different frequencies. In several embodiments, the reflected return signals are received by one or more receive antennas and processed to detect one or more targets. In various embodiments, the received signal can include a static (i.e. constant phase) signal corresponding to reflections from objects that do not move. The received signal can also include a phase varying signal that corresponds to reflections from a living target having measurable biometrics including (but not limited to) breathing patterns and heartbeats. In various embodiments, clutter (i.e. portions of the signal not corresponding to target reflections) is removed and the remaining portions of the received signal are analyzed for target detection. In a variety of embodiments, multiple antennas and multiple frequencies are utilized to create so-called sensing areas.

In one application, a life detecting radar ("FINDER") system can be utilized to locate victims buried within disaster rubble. In many embodiments, a CW radar is utilized to detect physical changes in a target such as (but not limited to) motion due to heartbeats and/or breathing. In many embodiments, targets can be detected by taking the raw radar data and performing range processing where stepped frequency data is taken and an inverse Fast Fourier Transform (FFT) applied to turn the frequency domain data into an equivalent time domain profile. In several embodiments, target Identification can be attempted to find unique targets in one or more beam and range bins by examining a band limited version of the signal for repetitive characteristics within the typical heart rate (and/or the respiration rate) utilizing a combination of autocorrelation and other methods which relies on the fact that while a given target's heart rate may vary, the general shape of their microwave cardiogram ("MCG") waveform does not (it merely stretches and shrinks). In various embodiments, a set of prototype waveforms can be produced which related to the normalized shape of a single heartbeat. In many embodiments, there is one set of data for each potential victim and data which identifies which beams/ranges that signal appears in. The set of data concerning each victim or target can also include data about the variability of that target.

Although FINDER is described in detail below as applied to detecting victims buried in rubble, it can have various other applications including (but not limited to) detecting prisoners barricaded in a prison, suspects hiding in farm fields or houses, as well being used as a form of diagnostic or biometric measurement instrument. Finder systems for detecting biometrics of and/or identifying a target in accordance with embodiments of the invention are further discussed below.

Life Detecting Radar ("FINDER") Systems

FINDER systems can be utilized to detect biometrics (i.e. physiological characteristics) of various targets. A FINDER system in accordance with an embodiment of the invention is illustrated in FIG. 1. The system 100 includes a user interface 102 configured to wirelessly connect and control at least one antenna unit 104, where the antenna unit transmits and receives radio signals as further described below. In several embodiments, the user interface 102 can also wirelessly connect to various other units including (but not limited to) computational assist units and data archiving units 106. In many embodiments, the user interface 102 can communicate wirelessly with a cellular data network 108 (i.e. wireless gateway) to connect to the Internet 110. Utilizing the Internet 110, the user interface 102 can access additional units including (but not limited to) a command post and other remote resources 112. Although described as separate units, in a variety of embodiments, the user interface 102 and the various units 104, 106 can be one physical unit communicating with each other via a direct network link or other means of data communication.

Figure 2:
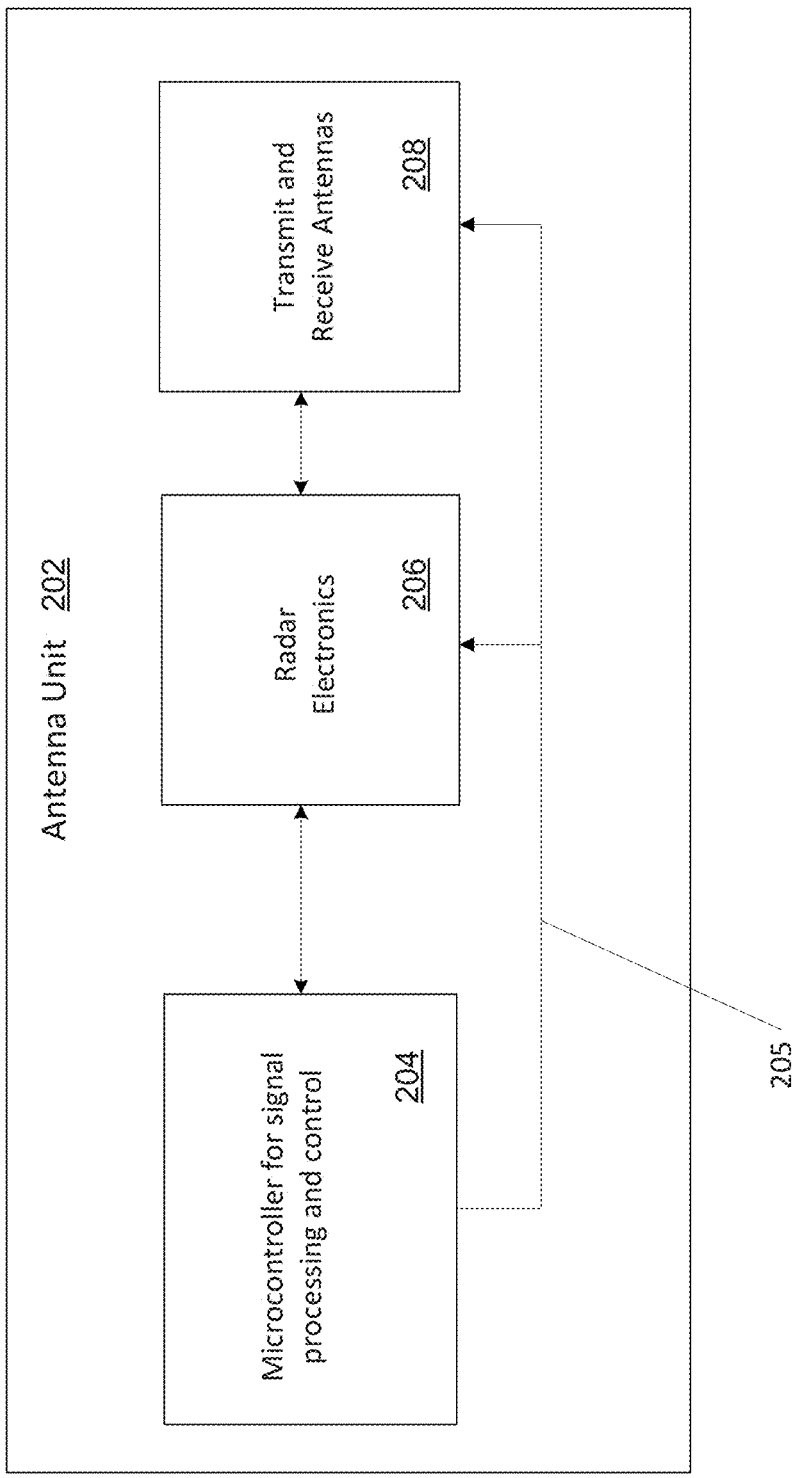
FIG. 2 illustrates an antenna unit in accordance with an embodiment of the invention.

As described above, a FINDER system can include one or more antenna units configured to transmit radio signals including (but not limited to) continuous wave signals and to receive reflected return signals. An antenna unit in accordance with an embodiment of the invention is illustrated in FIG. 2. The antenna unit 202 includes a microcontroller 204 that can send control signals 205 to radar electronics 206 and antennas 208 in connection with the microcontroller 204. In many embodiments, the antennas 208 include transmit antennas for transmitting radio signals as further discussed below. The antennas 208 can also include receive antennas for receiving return signals that include reflections from various physical objects in the search area as further discussed below. In various embodiments, the received signal is stored as digital radar data and transmitted to the microcontroller 204 for signal processing as further discussed below.

Figure 3A:
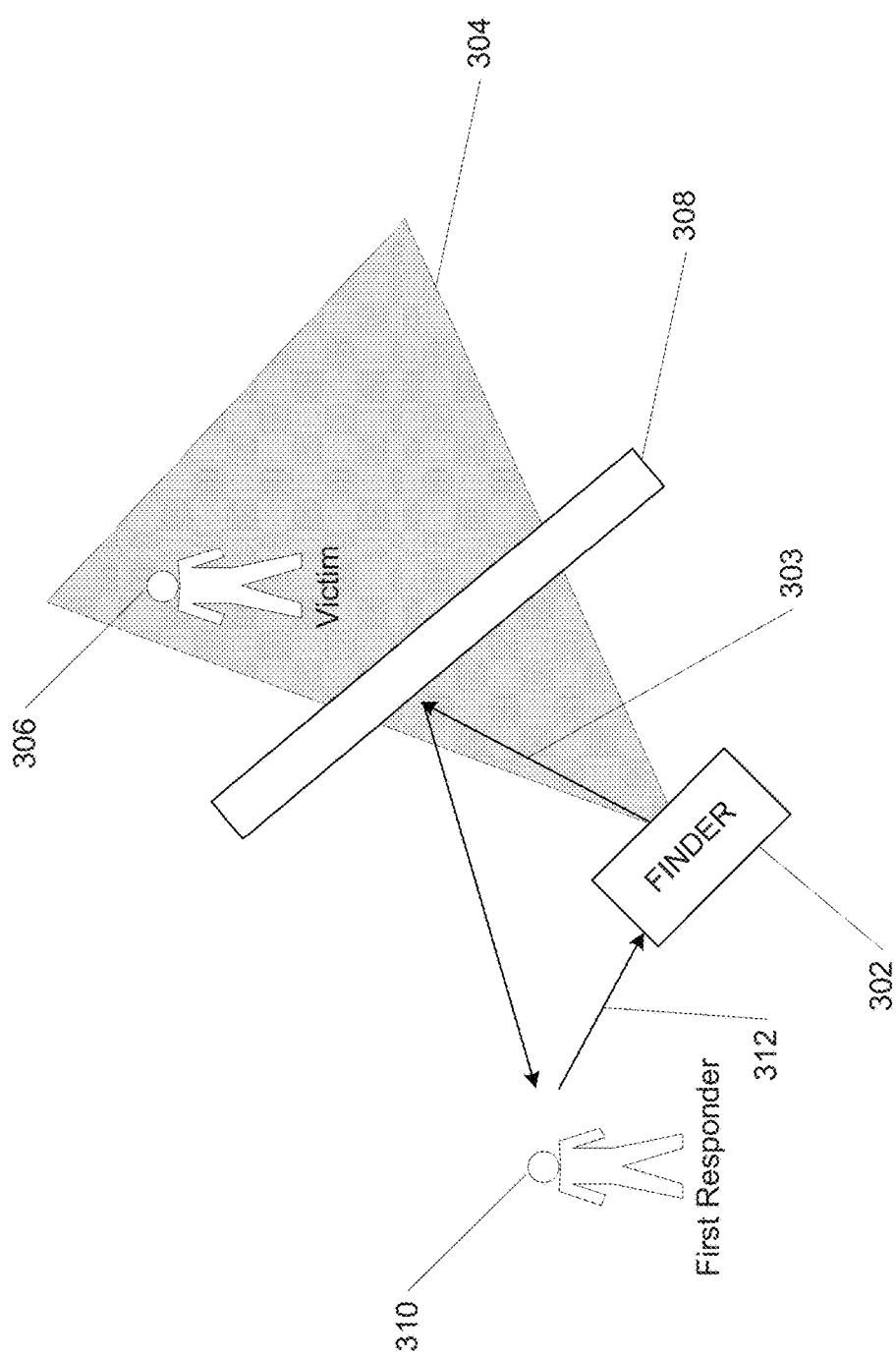
FIG. 3A illustrates a FINDER utilizing a single beam for detection in accordance with an embodiment of the invention.

The ability for a FINDER unit to form multiple beams can improve target identification and separation. A FINDER system utilizing a single beam for detection in accordance with an embodiment of the invention is illustrated in FIG. 3A. The FINDER unit 302 transmits signals to illuminate a single beam 304 to detect a victim 306 who is surrounded by rubble. Often in real life search scenarios, various objects 308 reflect the transmit signal 303 resulting in a return signal. Further, search personnel ("first responders") 310 can also cause return signals 312 (in this case reflections of other return signals) and be misidentified as victims.

Figure 3B:
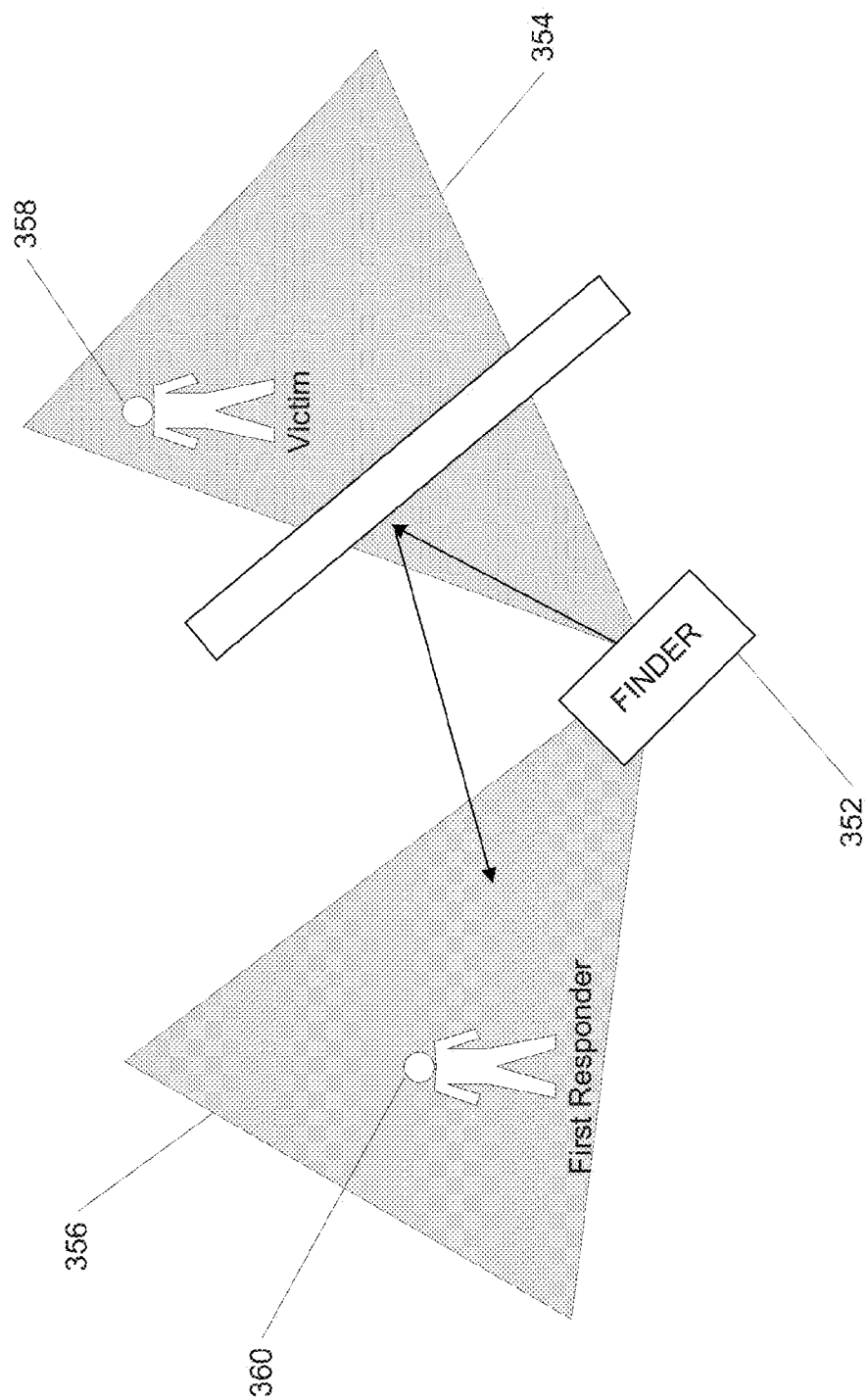
FIG. 3B illustrates a FINDER utilizing multiple beams for detection in accordance with an embodiment of the invention.

The use of multiple beams can increase detection accuracy and sensitivity. A FINDER system utilizing multiple beams for detection in accordance with an embodiment of the invention is illustrated in FIG. 3B. The FINDER unit 352 can form multiple beams 354 and 356 as further discussed below. The first beam 354 can detect the victim 358 while the second beam 356 can eliminate the first responder 360 as a possible victim as further discussed below. In addition, the ability to simultaneously "view" the search area in multiple directions can be useful. For example, being able to look in multiple directions at the same time allows rejection of phantom victims in the search area that are really just reflections from someone standing behind the FINDER antenna unit or next to the search area. In many embodiments, FINDER systems can be designed such that the basic radio frequency ("RF") signal chain is readily scalable to multiple beams and locations.

Figure 4A:
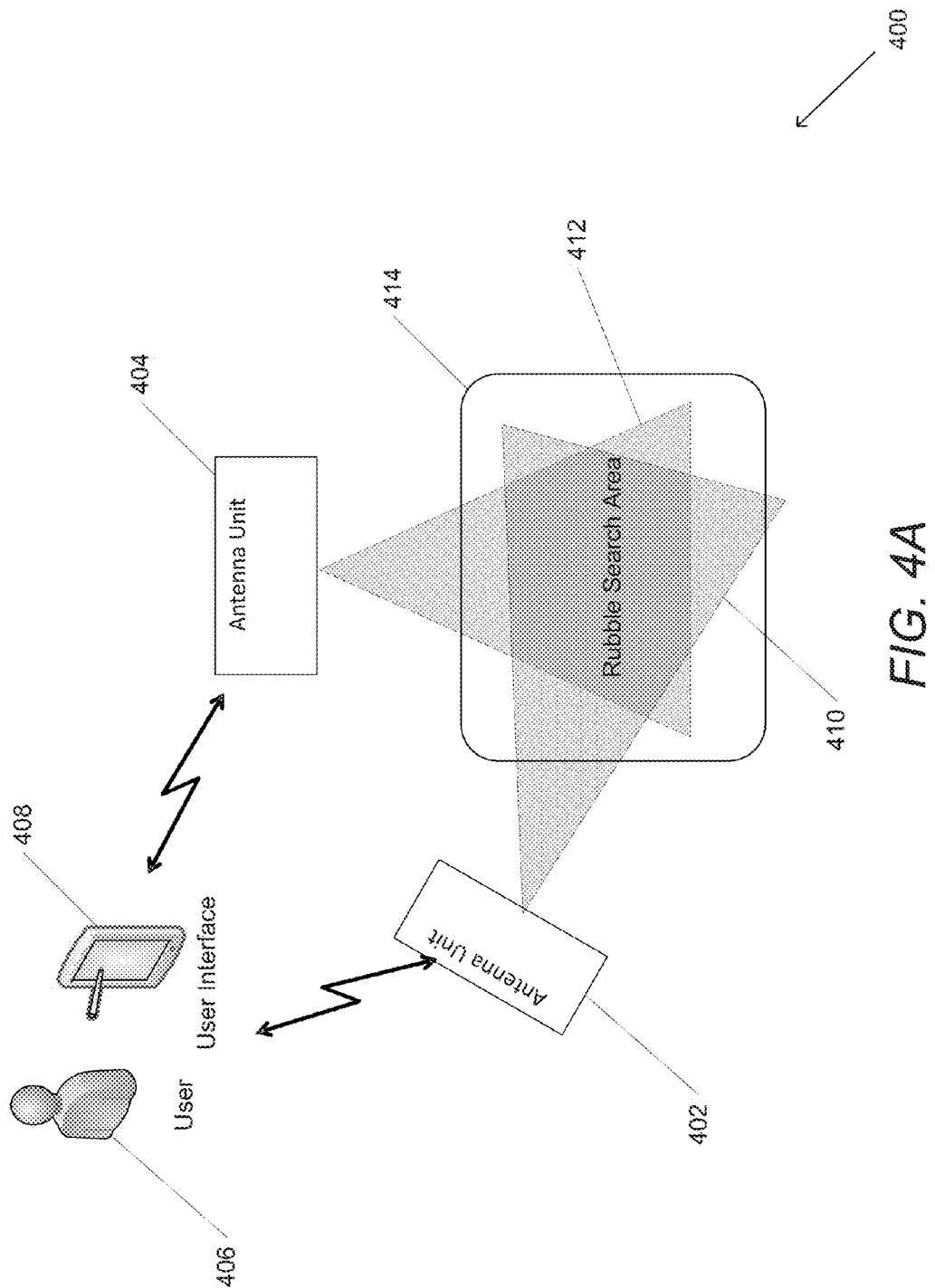
FIGS. 4A and 4B illustrate FINDER units utilizing multiple frequencies in accordance with an embodiment of the invention.
Figure 4B:
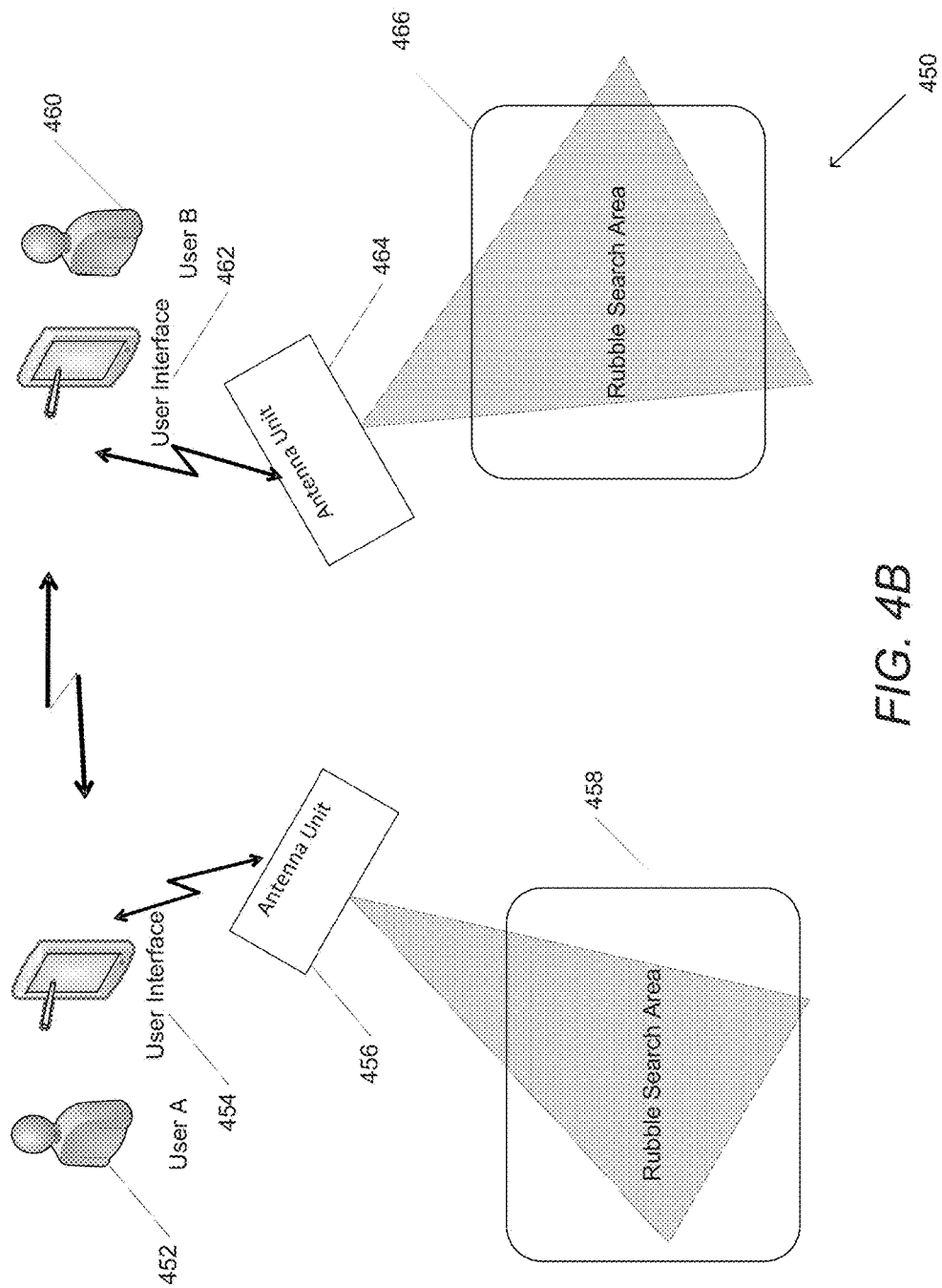

In addition to multiple beams, FINDER units can utilize multiple frequencies in an allocated bandwidth. FINDER units employing multiple frequencies can avoid interference by signals from other sources and/or not interfere with other systems by using a different frequency from such other systems. The use of multiple frequencies in accordance with an embodiment of the invention is illustrated in FIGS. 4A-B. The search scenario 400 illustrates two antenna units 402 and 404 being controlled by a single user 406 via a single user interface 408. The antenna unit 402 transmits a transmit signal to illuminate a beam 410 at a first frequency while antenna unit 404 transmits a separate transmit signal to illuminate a second beam 412 at a second frequency. Both beams 412 and 414 are transmitted to the same rubble search area 414 without interfering with each other because the two transmit signals operate at different frequencies. FINDER units utilizing multiple frequencies to illuminate two separate rubble search areas at the same location in accordance with an embodiment of the invention is illustrated in FIG. 4B. The search scenario 450 illustrates User A 452 utilizing a user interface 454 that communicates with an antenna unit 456 to illuminate a rubble search area 458 utilizing a first frequency. At the same location, User B 460 can utilize a user interface 462 to communicate with an antenna unit 464 to illuminate a rubble search area 466 using a second frequency. Again, the use of multiple frequencies allow for the FINDER units to avoid interfering with each other while operating in the same location. Furthermore, the detection of victims or targets can be enhanced by combining the outputs of multiple FINDER units to collect data concerning a target from multiple directions. In several embodiments, synchronized data recording can be utilized to enable the detection of matching time varying signals such as (but not limited to) respirations and heart beats in signals received by different antennas and/or FINDER units.

Although specific FINDER systems for detecting victims are discussed above with respect to FIGS. 1-4B, any of a variety of FINDER systems for detecting victims as appropriate to the requirements of a specific application can be utilized in accordance with embodiments of the invention. Signal processing for victim detection in accordance with embodiments of the invention are discussed further below.

Signal Characteristics and Signal Processing

FINDER systems utilize the principle of looking for small phase changes in a CW signal reflected from a victim. As a victim breathes, their body moves slightly (in particular, their chest wall on the order of 1 cm), and similarly, their heartbeat causes the abdominal surface and many other portions of the human body to move (on the order of 1 mm). The moving body causes reflections of transmit signals with varying phases (i.e. phase change). The detected phase change by receive antennas forms the basis of the so-called microwave cardiogram ("MCG"). Typically, each person has a unique MCG which varies depending on their orientation relative to the sensor, and, their physiological state. The uniqueness of MCG allows for the separation of combined MCGs from multiple targets (statistical analysis shows that it is unlikely that two people would have exactly the same heart rate, and even if the average rate were the same, the beat to beat variability is a random process, causing the two sequences to be uncorrelated). However, in real search scenario, there may be a multitude of other objects besides the victim reflecting a microwave signal back to the receiver, including (but not limited to) the rubble surrounding the victim, and objects near the radar. Typically, such signals are reflected from objects that are not moving and thus the phase stays relatively constant/static. The return signal that a radar receiver detects is typically a combination of a strong static signal component (corresponding to reflections from non-moving objects) that is unchanging with a weaker time varying signal component (corresponding to a victim). In terms of level, the static signal component that is received by the radar is typically on the order of 20 dB weaker than the transmitted signal, while the time varying return signal reflected off a victim is typically 60-100 dB (or more) weaker. The dominant reason for the weaker signal from the victim is the scattering of the signal in the rubble, more than the bulk attenuation in the rubble material.

Figure 5A:
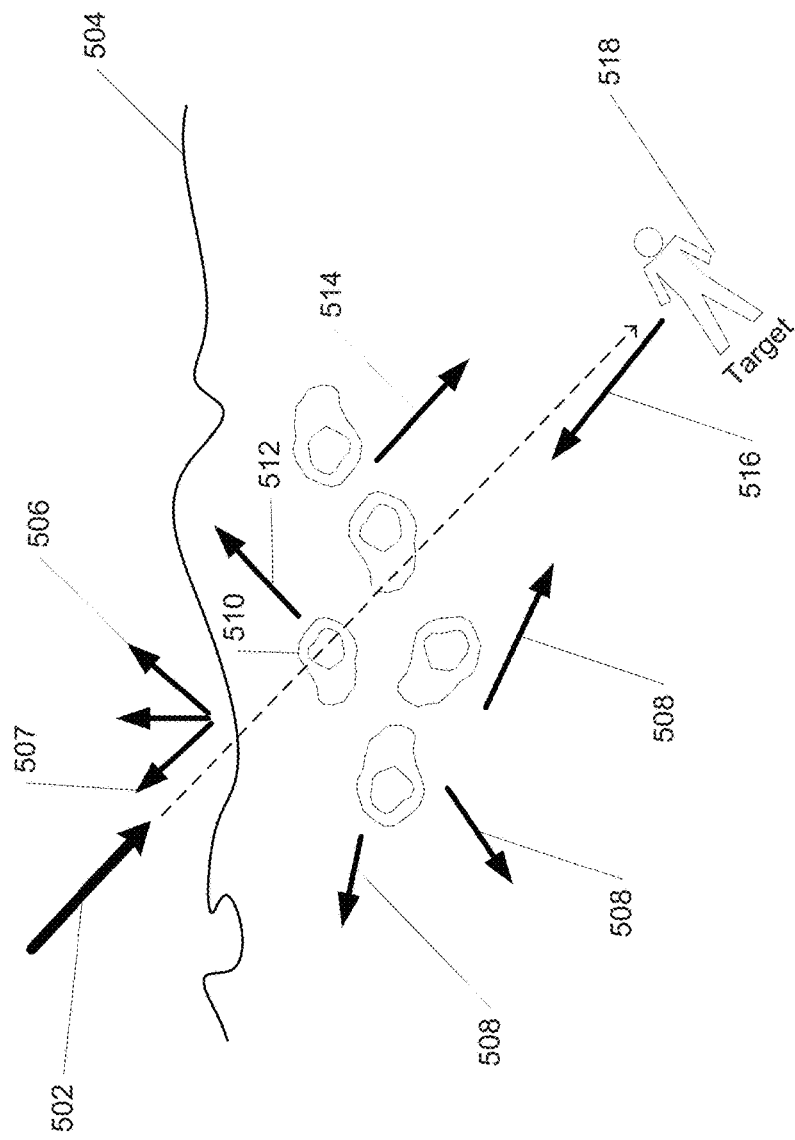
FIGS. 5A and 5B illustrate signal propagation characteristics of a signal generated by a FINDER unit in accordance with an embodiment of the invention.
Figure 5B:
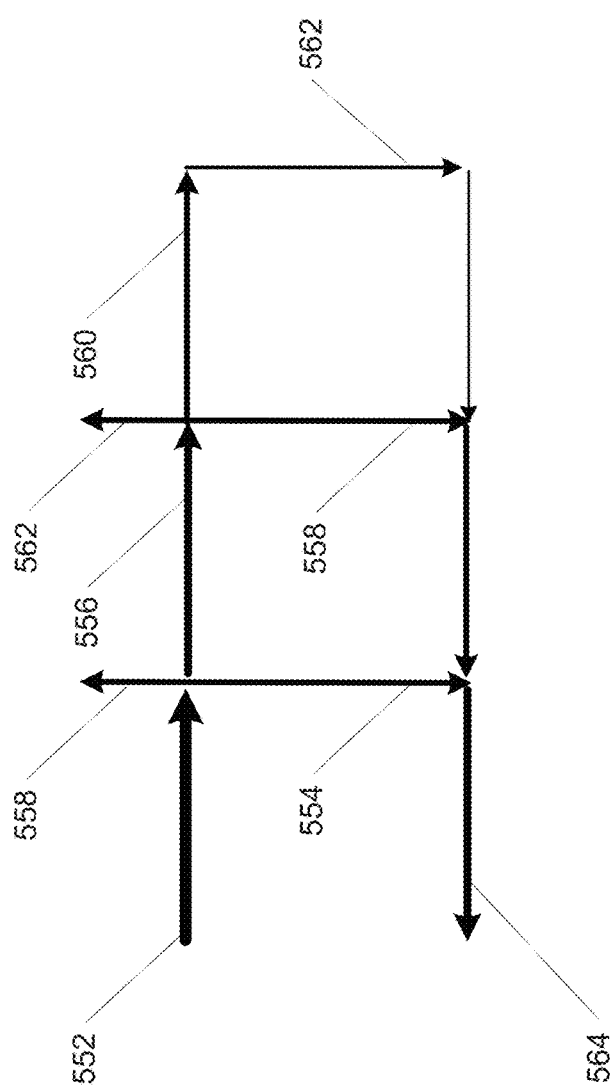

Signal propagation characteristics in accordance with an embodiment of the invention are illustrated in FIGS. 5A-B. In many embodiments, a transmit signal 502 in a frequency band such as (but not limited to) 3.1-3.4 GHz can hit a surface 504 causing surface scatter with portions that scatter away 506 and portions that reflect back 507 to the radar. In several embodiments, portions of the transmit signal (and any reflected signals) can be absorbed and lost into the soil 508. Further, rubble 510 can cause rubble scatter, again, with portions reflecting back toward the radar 512, portions directing toward the target 514, and portions that scattered away. A buried target 518 can also cause a target reflection that includes portions that reflect toward the radar 516, portions that are loss due to soil absorption, and/or scatter away. FIG. 5B illustrates the cumulative effects of reflections of a transmitted signal. The transmitted signal 552 first hits a surface causing surface scatter back toward the radar 554, toward the target 556, and away 558. Rubble in the search area can cause rubble scatter toward the radar 558, toward the target 560, and away 562. Further, a target causes a target reflection toward the radar 562. The cumulative signal of the reflections back towards the radar is received by a receive antenna at the received signal 564. Generally, portions of all signals (signals that return toward the radar or continue towards the victim) can be lost to the soil and/or scattered away.

In many embodiments, contributions to the received signal that are not the result of target reflections can be characterized as clutter and removed via a cancellation path. In various embodiments, the cancellation path includes subtracting a sample of the transmitted signal from the received signal where the sample signal's phase and amplitude are adjusted to closely match the static unvarying clutter signal. In many embodiments, the transmitted signal that is cancelled from the received signal is not the signal actually transmitted by the finder unit, but can be a signal received by the finder unit from a direction that does not include the search area. Therefore, the transmitted signal can be considered to be any signal that enables cancellation of environmental reflections from areas outside of the search area. Typically, when the sample signal is subtracted from the received signal, only a varying signal from the victim(s) remains and can be further processed for biometric analysis and victim detection. In several embodiments, the cancellation path can be automatically adjusted utilizing software.

Although specific signal characteristics and signal processing methods for detecting victims are discussed above with respect to FIGS. 5A-B, any of a variety of signals and processing of signals for detecting victims as appropriate to the requirements of a specific application can be utilized in accordance with embodiments of the invention. FINDER units capable of discriminating between spurious and intended targets in accordance with embodiments of the invention are discussed further below.

Target Separation

Spurious targets (i.e. not intended targets) can be a problem in detecting victims in a search area. As discussed above, a person standing to the side of the search area can show up as a target, because the antenna's response does not fall off very quickly. Typically, spurious targets show up as a very strong signal because their reflection are not attenuated and scattered by passing through the rubble. In many embodiments, multiple beams can be utilized to simultaneously look in multiple directions, including to the side and rear of a FINDER. Further, a target that is not within the sensing area of a particular receive antenna may be detected by other receive antennas, and, may even produce a stronger reflection signal in those directions allowing it to be identified and separated out. Likewise, multiple frequencies can be useful as reflected and side targets tend not to be as scattered and thus showing up as narrower time domain responses.

Figure 6:
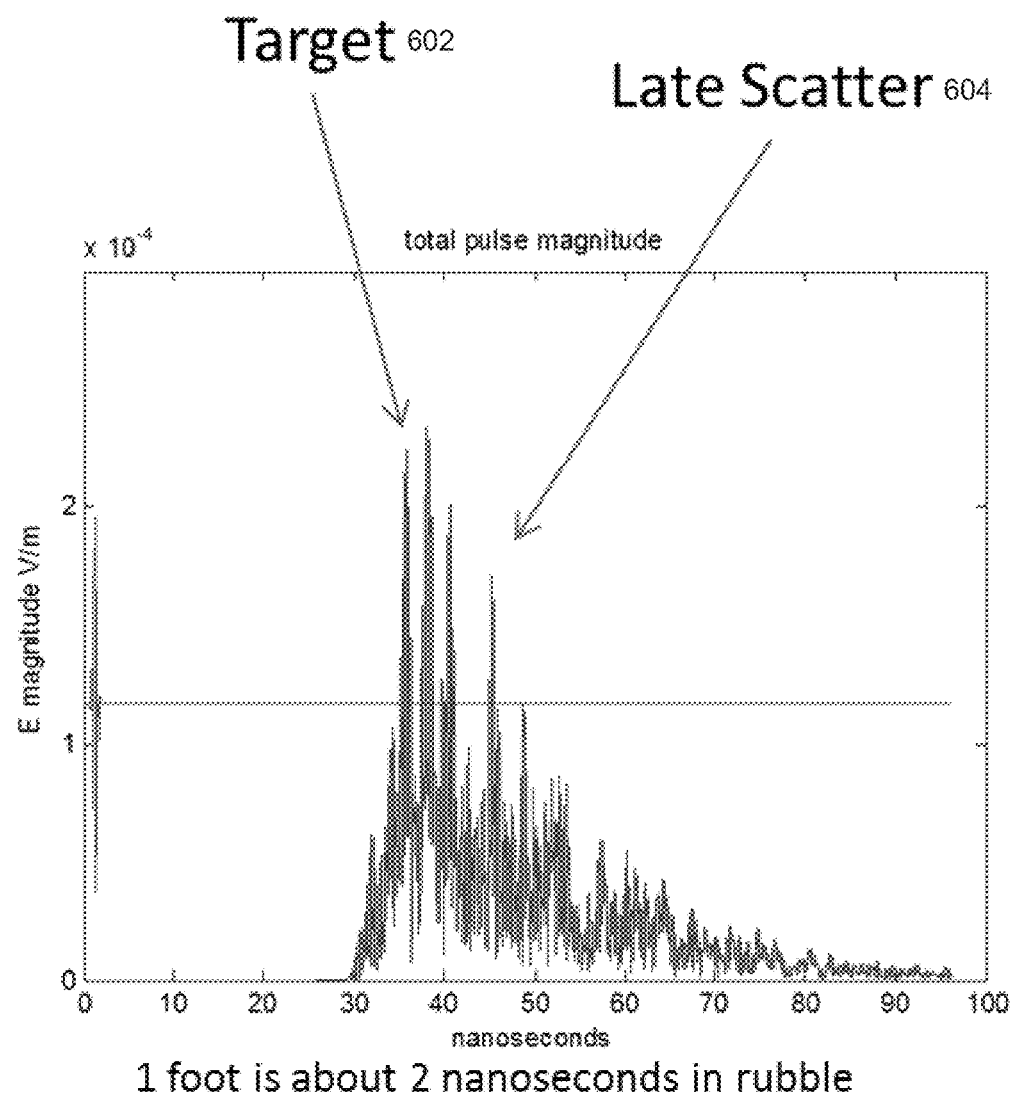
FIG. 6 is a graph illustrating time domain response of a received signal in accordance with an embodiment of the invention.

A graph illustrating a time domain response in accordance with an embodiment of the invention is illustrated in FIG. 6. The graph 600 depicts spikes of magnitude at various times corresponding to reflections from a target 602 and late scatter 604. In many embodiments, a two nanosecond delay corresponds to one foot of rubble.

Figure 7:
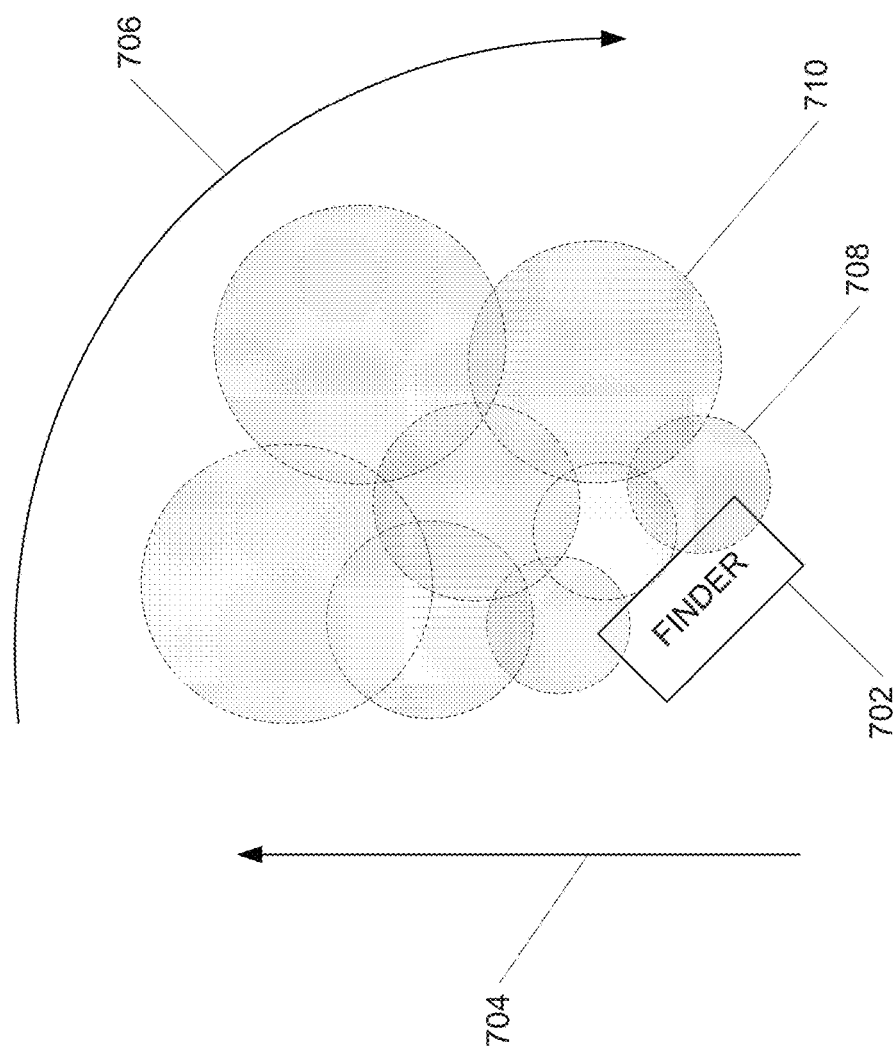
FIG. 7 illustrates sensing areas of a FINDER unit in accordance with an embodiment of the invention.

As discussed above, a FINDER unit can divide a search area into multiple sensing areas in different directions and distances. Various sensing areas in accordance with an embodiment of the invention are illustrated in FIG. 7. The FINDER unit 702 can have a range 704 and sweeping direction 706 defining different sensing areas such as 708 and 710. Typically, targets will show up in multiple sensing areas, but will be stronger or more sharply defined in some areas than in others. In processing the received signals, the sensing areas directly in front of the FINDER unit and the targets which have levels and characteristics consistent with being the intended target can be presented to a user. In many embodiments, the FINDER uses multiple antennas for multiple beams and a limited stepped frequency CW radar techniques for multiple range zones.

Figure 8:
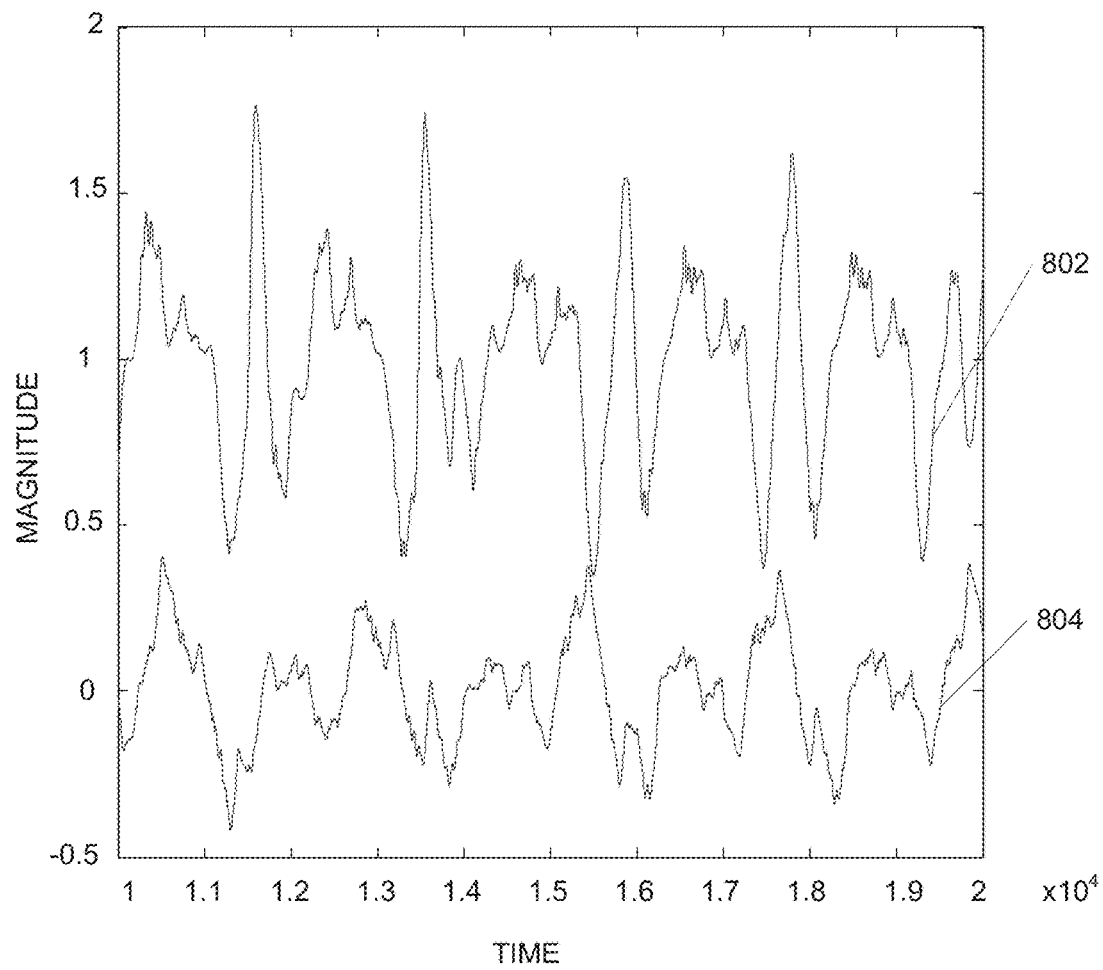
FIG. 8 is a graph illustrating microwave cardiogram ("MCG") recorded from two subjects in accordance with an embodiment of the invention.

The FINDER can also discriminate among targets since each person typically has a unique MCG and respiration related reflection signals. A graph illustrating MCG recorded from two subjects in accordance with an embodiment of the invention is illustrated in FIG. 8. The graph 800 shows approximately 10 seconds of MCGs recorded from two different subjects. While both the first signal 802 and the second signal 804 are rhythmic and periodic, both signals are quite different and readily distinguishable.

Although specific target discrimination techniques utilizing multiple sensing areas are discussed above with respect to FIGS. 6-8, any of a variety of target discrimination techniques utilizing multiple sensing areas as appropriate to the requirements of a specific application can be utilized in accordance with embodiments of the invention. Data collection and signal processing techniques in accordance with embodiments of the invention are further discussed below.

Data Collection and Signal Processing

Figure 9:
FIG. 9 is a timing diagram for a data collection process in accordance with an embodiment of the invention.

During data collection, FINDER systems can make a series of measurements, selecting a beam and frequency for each measurement. In post processing, the recorded data can be grouped by various search/sensing areas where each area is analyzed for target detection. A timing diagram for a data collection process in accordance with an embodiment of the invention is illustrated in FIG. 9. In many embodiments, a microcontroller sends frequency and beam selection signals 902, where a short delay to stabilize is followed by the received signals being digitized for further processing. The configuration 900 utilizes two antennas 902 and 904 for beam selection. An "up" trigger indicates an antenna as selected and active, whereas a "down" trigger indicates that the antenna is not selected. The frequency selection 906 indicates when a voltage controlled oscillator ("VCO") frequency has settled (indicated by an "up" trigger) and sampling triggered 910. The basic operation cycle is the period when a new load signal is processed to the when the next load signal is processed.

In many embodiments, rapidly switching among beams and frequencies allows multiple measurements to be made during a short enough time such that the heartbeat and/or respiration signals are essentially unchanging. When making multiple measurements in a short period of time, data should be collected at a rate sufficient to perform processing. In various embodiments, FINDER systems collect samples for each search area at a sampling rate between 200-1000 Hz. In several embodiments, to resolve a 20 meter search range into range zones of approximately 2 meters each, FINDER typically utilizes at least 10 frequencies. With medium gain antennas having a beam width on the order of 70 degrees, 360 degrees can be covered with 8 beams, arranged in the cardinal directions.

Figure 10:
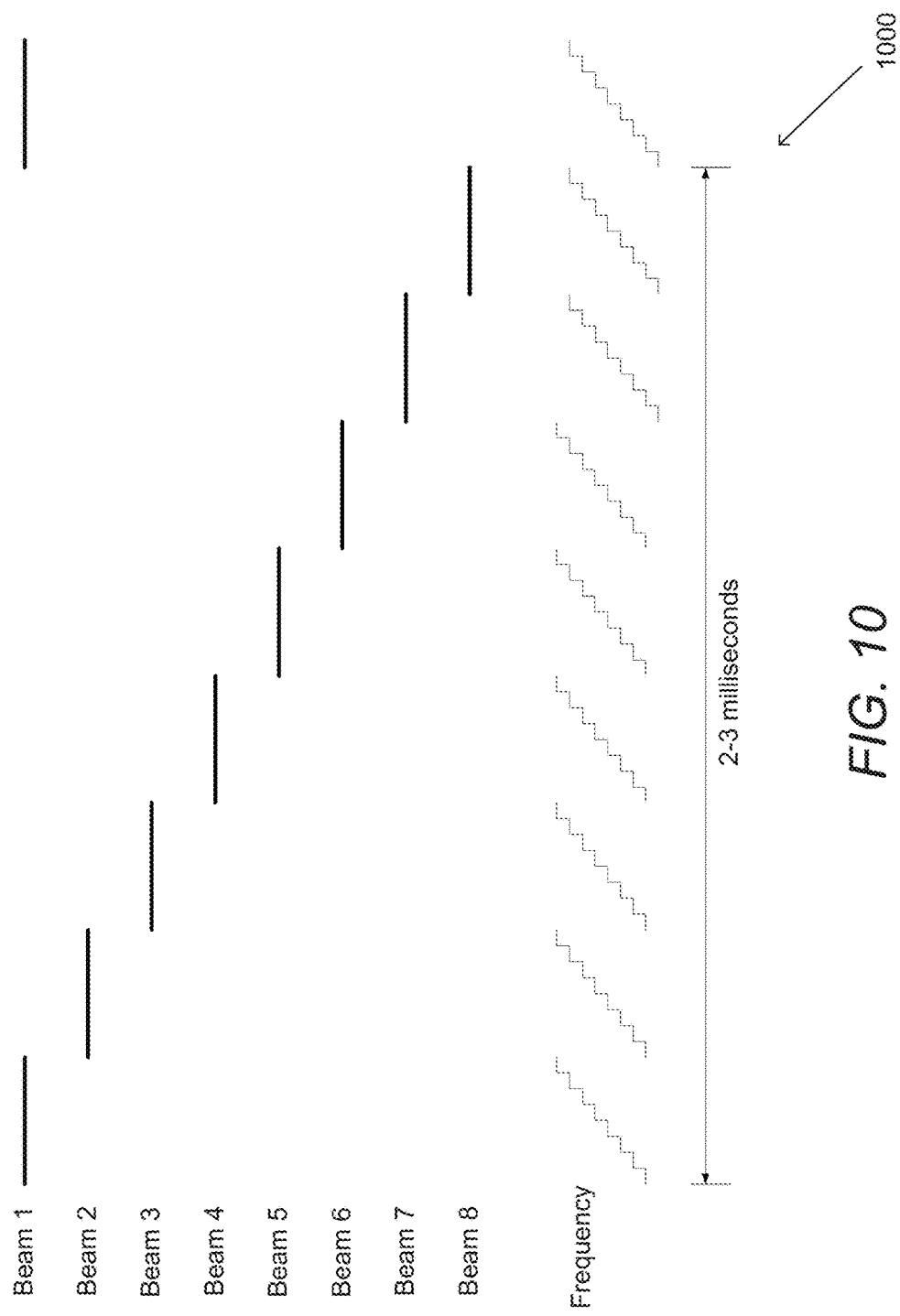
FIG. 10 is timing diagram for a round robin time sharing in accordance with an embodiment of the invention.

A round robin time sharing strategy for cycling between beams and frequencies in accordance with an embodiment of the invention is illustrated in FIG. 10. The graph 1000 includes 8 separate beams where all frequencies are used for each beam in sequence. In various embodiments, other patterns for beam and frequency combinations can be utilized, including where all beams could be measured at each frequency, with frequency stepping slower than the beam.

In many embodiments, the time for the FINDER hardware to change frequencies and/or beams is typically much faster than the time to collect the data samples. For example, if one complete cycle scan time takes approximately 3 milliseconds (300 Hz revisit rate between beam/frequency), to cover all possible combinations of the 80 frequencies and beams (10 frequencies×8 beams), FINDER can spend approximately 37 microseconds at each dwell. At a sample rate of 500 Hz (2 ms per cycle) the dwell at each beam/frequency combination is reduced to 25 microseconds. Such short dwell times can present a problem with sampling the data quickly enough. Further, to reduce the amount of noise, the signal is low pass filtered at approximately 10 kHz. However, a 10 kHz filter typically utilizes a minimum of several hundred microseconds at each dwell to account for the signal delay through the filter. The modular FINDER design can resolve this fundamental conflict between "fast enough to make all the measurements often enough" and "slow enough to make good measurements at each point" by making multiple measurements at the same time. In several embodiments, FINDER systems can use multiple radio frequency ("RF") modules and an antenna switching matrix to make multiple measurements at the same time, with switching and frequency pattern chosen to prevent the same frequency from being used on two beams at the same time.

Figure 11:
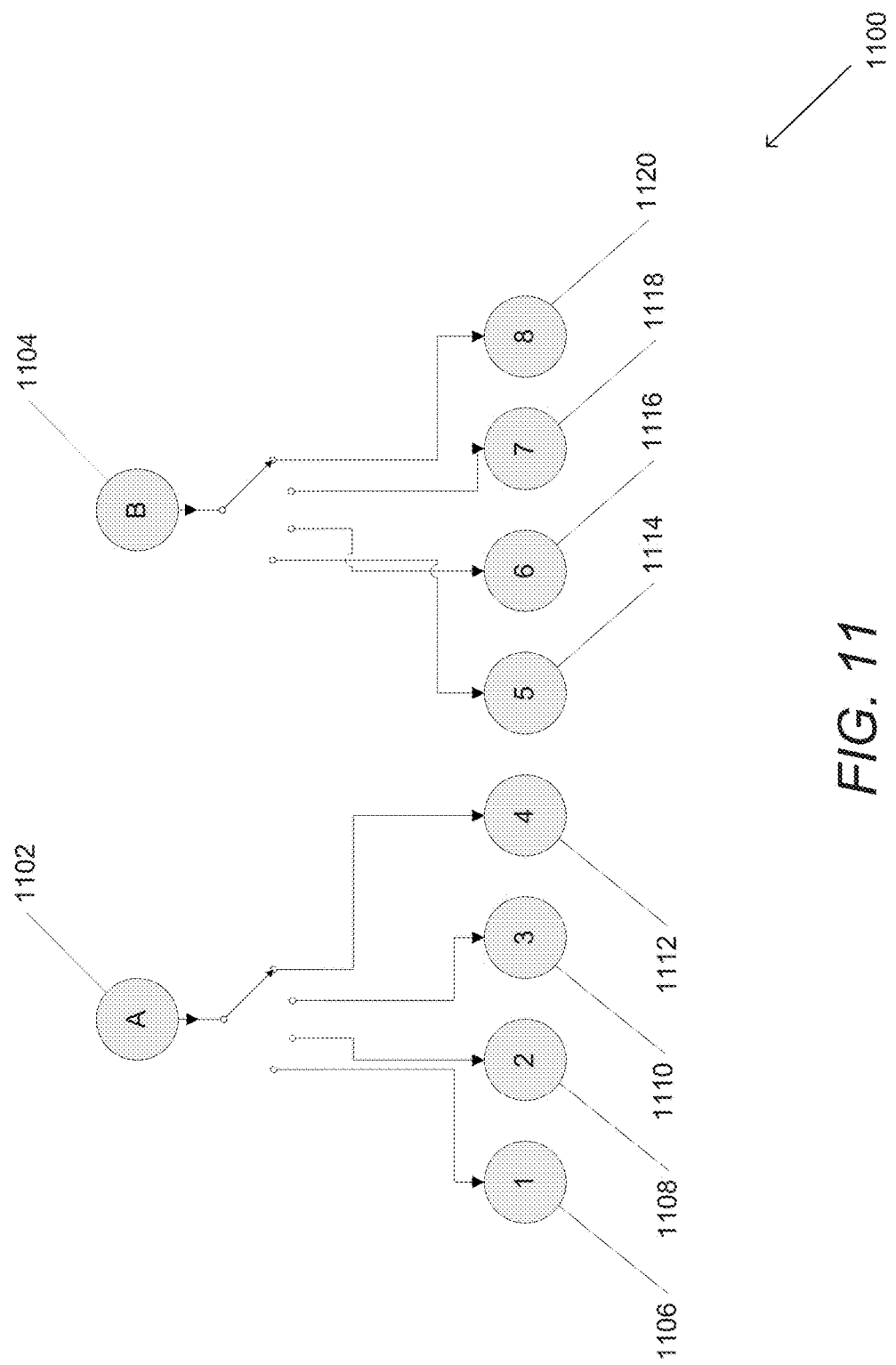
FIG. 11 is a schematic diagram illustrating two radio frequency ("RF") modules and eight antennas in accordance with an embodiment of the invention.

A block diagram illustrating two RF modules configured to utilize eight antennas in accordance with an embodiment of the invention is illustrated in FIG. 11. The system 1100 includes two RF modules 1102 and 1104 that collect data using eight antennas via a pair of four way switches. The RF module 1102 utilizes antennas 1106, 1108, 1110, and 1112 and RF module 1104 utilizes 1114, 1116, 1118, and 1120. In many embodiments, a FINDER unit can share antennas by using different frequencies on the same antenna, and/or a more sophisticated switching network can be realized to allow selection of multiple antennas at one time. Although RF modules with specific numbers of antennas are described above with respect to FIG. 11, a variety of RF modules including those with varying numbers of antennas as appropriate to a specific application can be utilized in accordance with embodiments of the invention.

Figure 12:
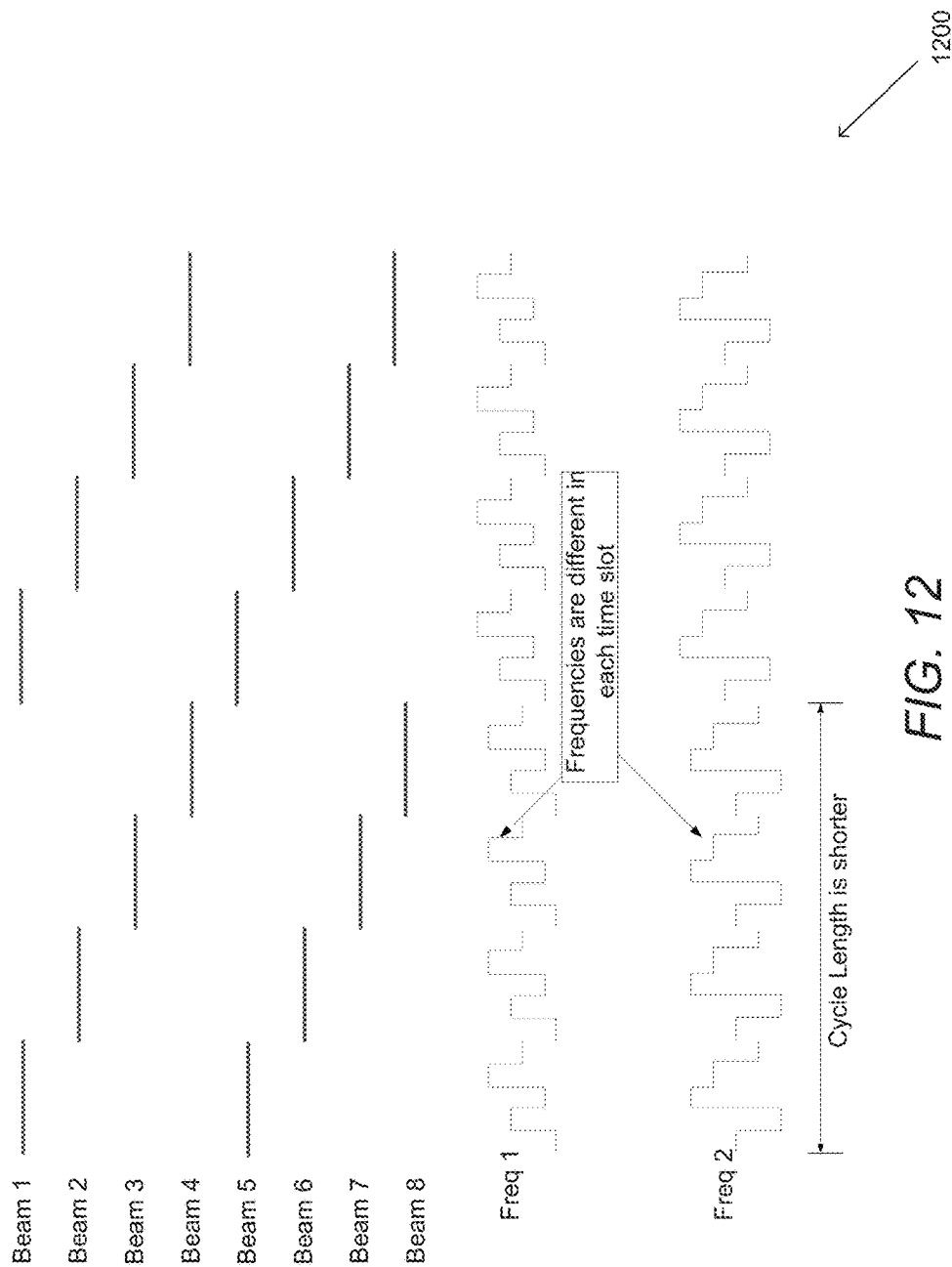
FIG. 12 is a cyclical timing diagram of a life detecting radar utilizing two RF modules and eight antennas in accordance with an embodiment of the invention.

In several embodiments, the selection of multiple antennas for a single measurement allows for synthesizing a narrower beam. A timing diagram corresponding to system 1100 illustrated in FIG. 11 is illustrated in FIG. 12. The timing diagram 1200 illustrates each unit (beam) utilizing different frequencies at any given time (i.e. the frequencies are different in each time slot). As discussed above, a further reason for the ability to change frequencies is to avoid frequencies which cause interferences. For example, if there are multiple FINDER units in the field, the sequence and choice of frequencies can be coordinated among the units. One possible coordination method could be where each FINDER knowing the current time can combine its unique serial number and the current time to generate a unique and thus non-interfering sequence of frequencies.

Although specific data collection and signal processing techniques are discussed above with respect to FIGS. 9-12, any of a variety of data collection and signal processing techniques as appropriate to the requirements of a specific application can be utilized in accordance with embodiments of the invention. FINDER system units in accordance with embodiments of the invention are further discussed below.

Hardware Architecture and Design

FINDER systems typically include a user interface unit and an antenna unit as discussed above. In many embodiments, the two units can communicate by a standard wireless network including (but not limited to) IEEE 802.11 WiFi standard, and/or Bluetooth. The user interface unit can be any standard ruggedized field suitable touch pad computer such as the Panasonic Toughbook H2, although almost any PC with an appropriate wireless link, sufficient internal storage for the data, and standard browser functionalities would suffice. The antenna unit can include antennas (transmit and receive), at least one RF module, digital circuitry to control the RF modules and gather data. In several embodiments, the antenna unit can also include support infrastructure such as (but not limited to) a GPS receiver, a camera, and a network interface. A FINDER system can include multiple user interface units, multiple antenna units, and additional support units that communicate with each other using various wireless network standards. In many embodiments, data including (but not limited to) control signals and received signal data, pass between units using standard network protocols such as TCP/IP and UDP/IP and/or secured protocols such as HTTPS and SSH.

Figure 13:
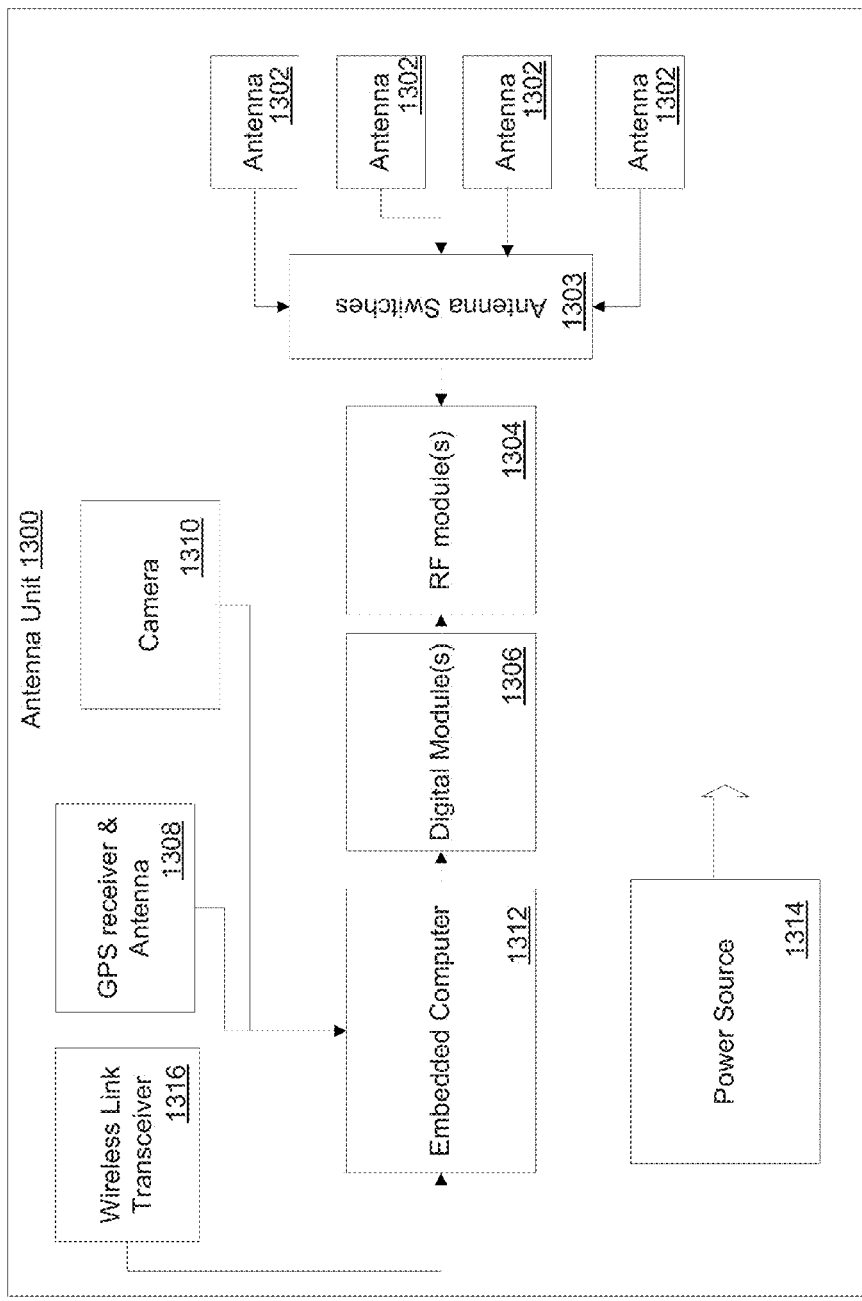
FIG. 13 is a block diagram illustrating an antenna unit in accordance with an embodiment of the invention.

A block diagram of an antenna unit in accordance with an embodiment of the invention is illustrated in FIG. 13. The antenna unit 1300 includes four antennas 1302 connected to an antenna switch 1303 that is connected to an RF module 1304. In many embodiments, the RF module is also connected to a digital module 1306 that are connected to an embedded computer (i.e. microcontroller) 1312. The embedded computer can also be connected to additional devices such as (but not limited to) a GPS receiver and antenna 1308 and camera 1310. The antenna unit typically includes a power source 1314 and can communicate to the user interface (and other units) via a wireless link transceiver 1316. While the antenna unit 1300 illustrates a single digital module and single RF module, with an antenna switch connecting 4 antennas, in many embodiments, FINDER can utilize multiple modules and various numbers of antennas. In many applications, the primary factor driving the selection criteria of components can be the desired measurement performance and speed as discussed above (i.e. FINDER will need to search in enough directions with enough range resolution to be able to remove ambiguities). This is dependent to a certain extent on physical packaging of the antennas (which can affect their beam patterns) and the responses to actual rubble environments (which typically can't be known until measured with multiple beams).

Figure 14A:
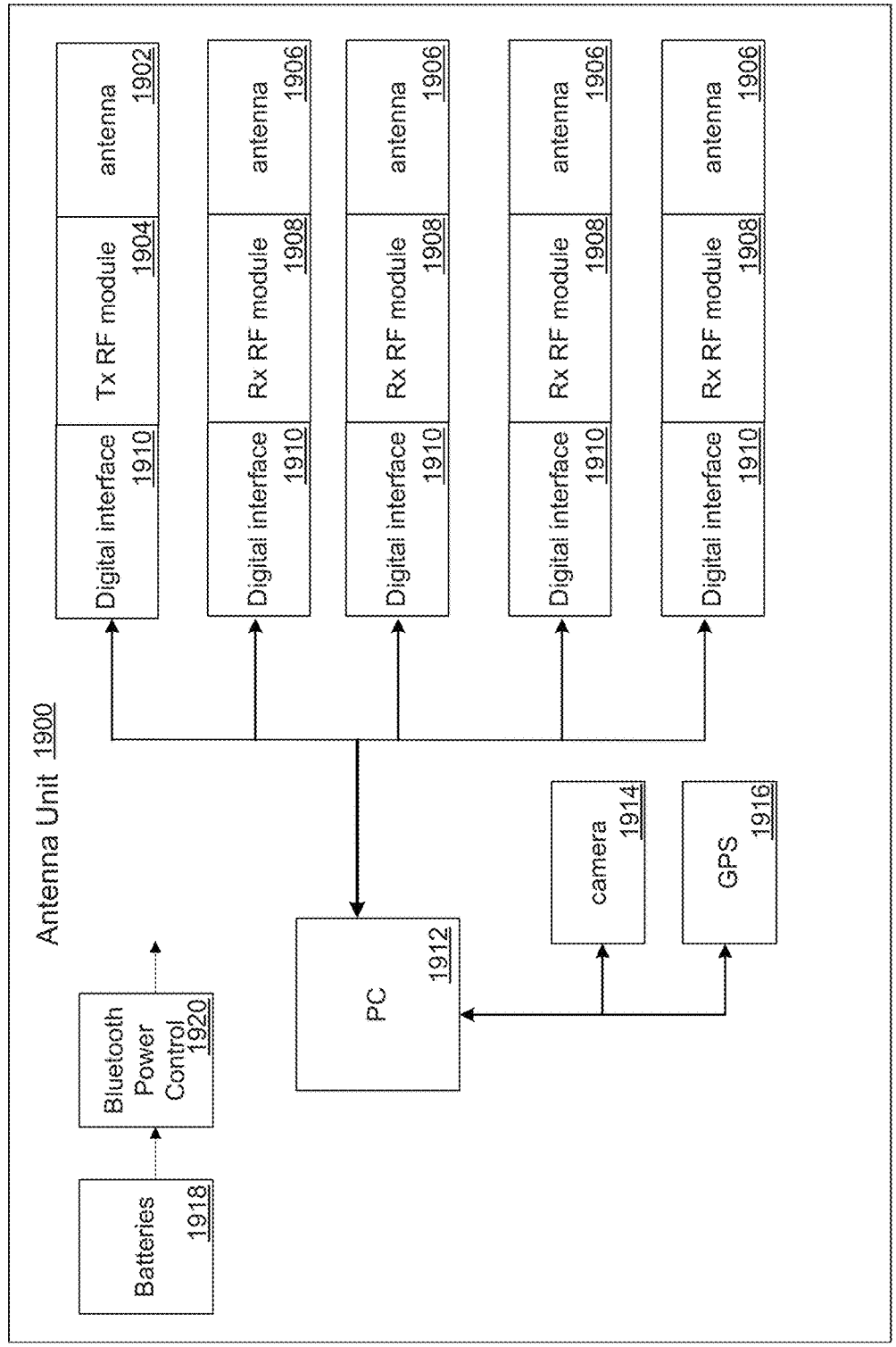
FIG. 14A is a block diagram illustrating an antenna unit with one transmit RF and four receive RF modules in accordance with an embodiment of the invention.
Figure 14B:
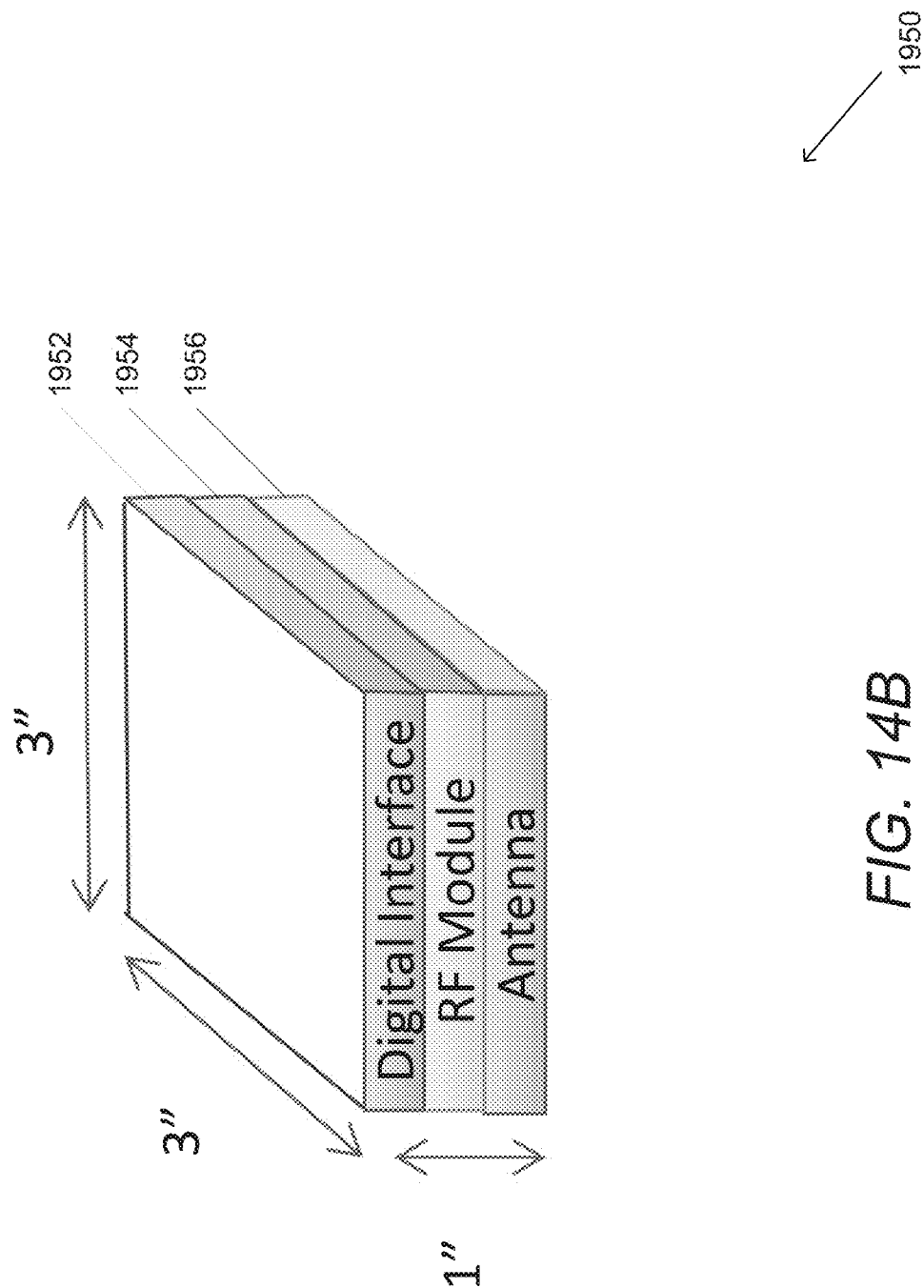
FIG. 14B is a design concept of a module of an antenna unit with one transmit RF and four receive RF modules in accordance with an embodiment of the invention.

A block diagram of an antenna unit in accordance with an embodiment of the invention is illustrated in FIG. 14A. The antenna unit 1900 includes one transmit antenna 1902 connected to a transmit RF module 1904 and four receive antennas 1906 each connected to a receive RF module 1908. The transmit and receive RF modules perform transmitter and receiver functions, respectively, as further described below. In many embodiments, the RF modules are connected to various digital interfaces 1910 that interface with an embedded computer 1912 for receiving control signals and/or transferring collected radar data. In a variety of embodiments, the digital interfaces act as the digital modules as described above and further described below. In various embodiments, the embedded computer 1912 is connected to a camera 1914 for collecting digital image data of a search site. In addition, the embedded computer 1912 can be connected to a GPS 1916 receiver/transmitter for accessing position and time data. As described above, the antenna unit 1900 can be wireless connected to a user interface unit. In several embodiments, the antenna unit 1900 can also include a power source 1918 (such as but not limited to batteries) and power controls for wireless communication capabilities. A modular design concept of an antenna, RF module, and digital interface in accordance with an embodiment of the invention is illustrated in FIG. 14B. The modular unit 1950 includes stacking of the digital interface 1952 on top of the RF module 1954 which can be stacked on top of the antenna 1956. In several embodiments, the modular unit is three inches in width, three inches in length, and one inch thick. Although specific stacking arrangements and dimensions are described, a variety of arrangements and dimensions can be utilized in accordance with embodiments of the invention.

Although specific user interface and antenna units are discussed above with respect to FIGS. 13-14B, any of a variety of user interface and antenna units as appropriate to the requirements of a specific application can be utilized in accordance with embodiments of the invention. Antenna configurations in accordance with embodiments of the invention are further discussed below.

Antenna Configurations

Figure 15:
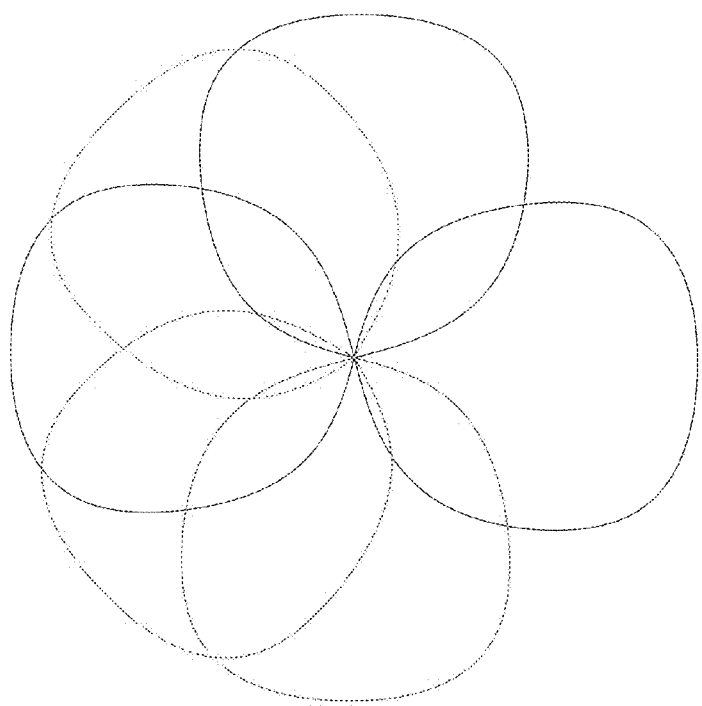
FIG. 15 is an arrangement of antenna beams in accordance with an embodiment of the invention.

In many embodiments, antennas can be patch radiators designed to match the frequency of use of the FINDER units (e.g. in the 3.1-3.4 GHz band). Analysis of reflected signals from rubble and a victim show that the rubble serves as a very effective polarization randomizer, such that the antennas are all typically polarized the same way. A basic patch with 6-8 dBi gain will have a half power beamwidth on the order of 70-80 degrees and thus cover the 360 degree span around an antenna unit with 8 beams. An arrangement of antenna beams in accordance with an embodiment of the invention is illustrated in FIG. 15. The antenna arrangement 1400 shows an example arrangement of beams (not all beams are shown for clarity). In many embodiments, coupling between adjacent antennas is expected to be less than −20 dB, since each are spaced more than a wavelength distance apart.

Figure 16A:
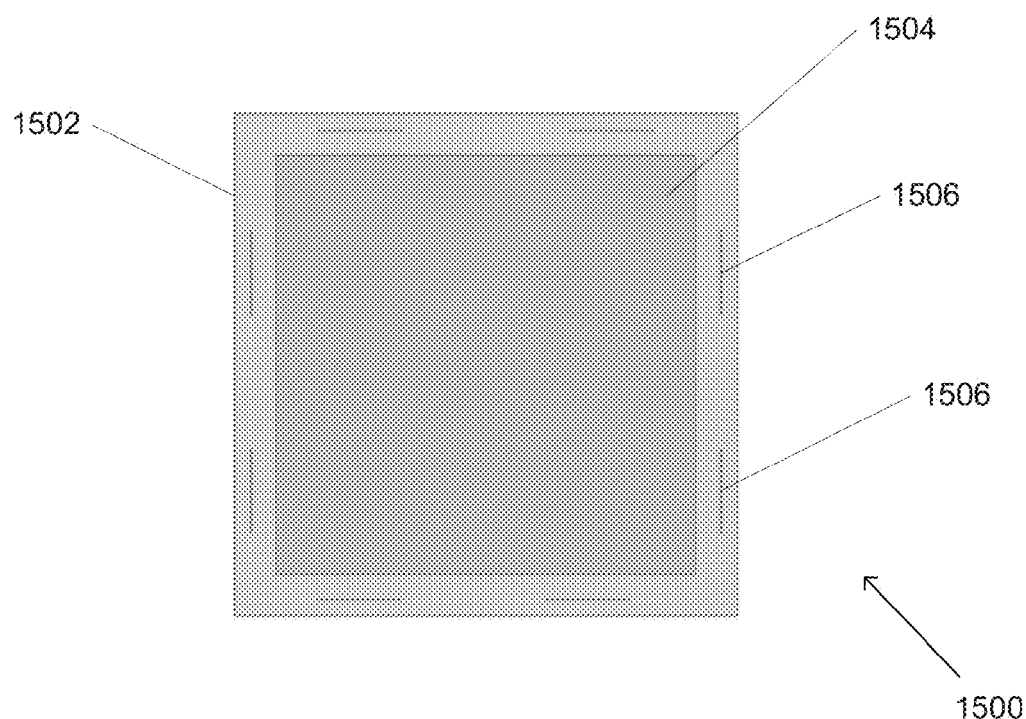
FIGS. 16A-C illustrate embodiments of antenna units with patch radiator antennas in accordance with an embodiment of the invention.
Figure 16B:
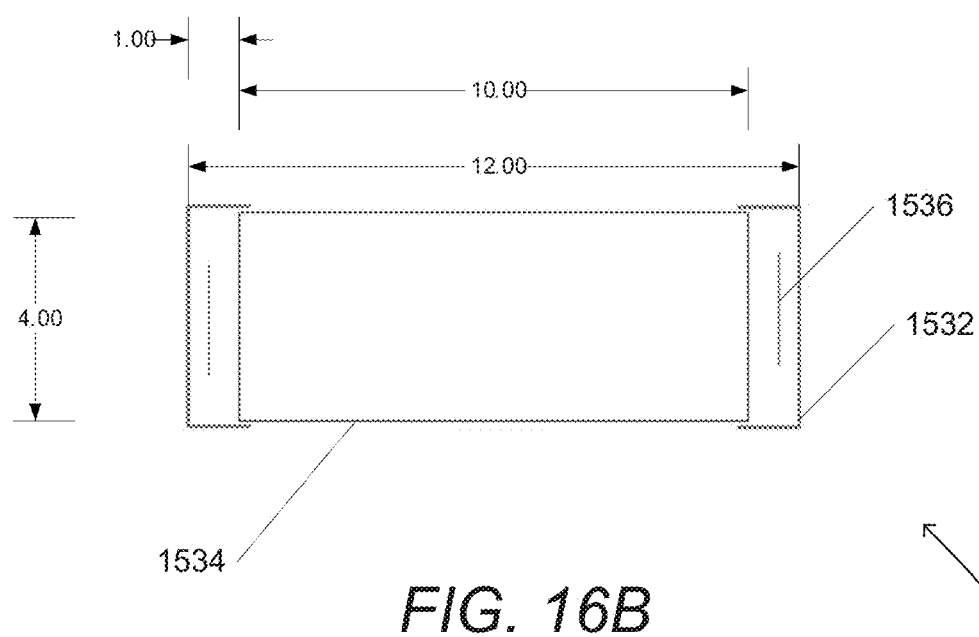
Figure 16C:
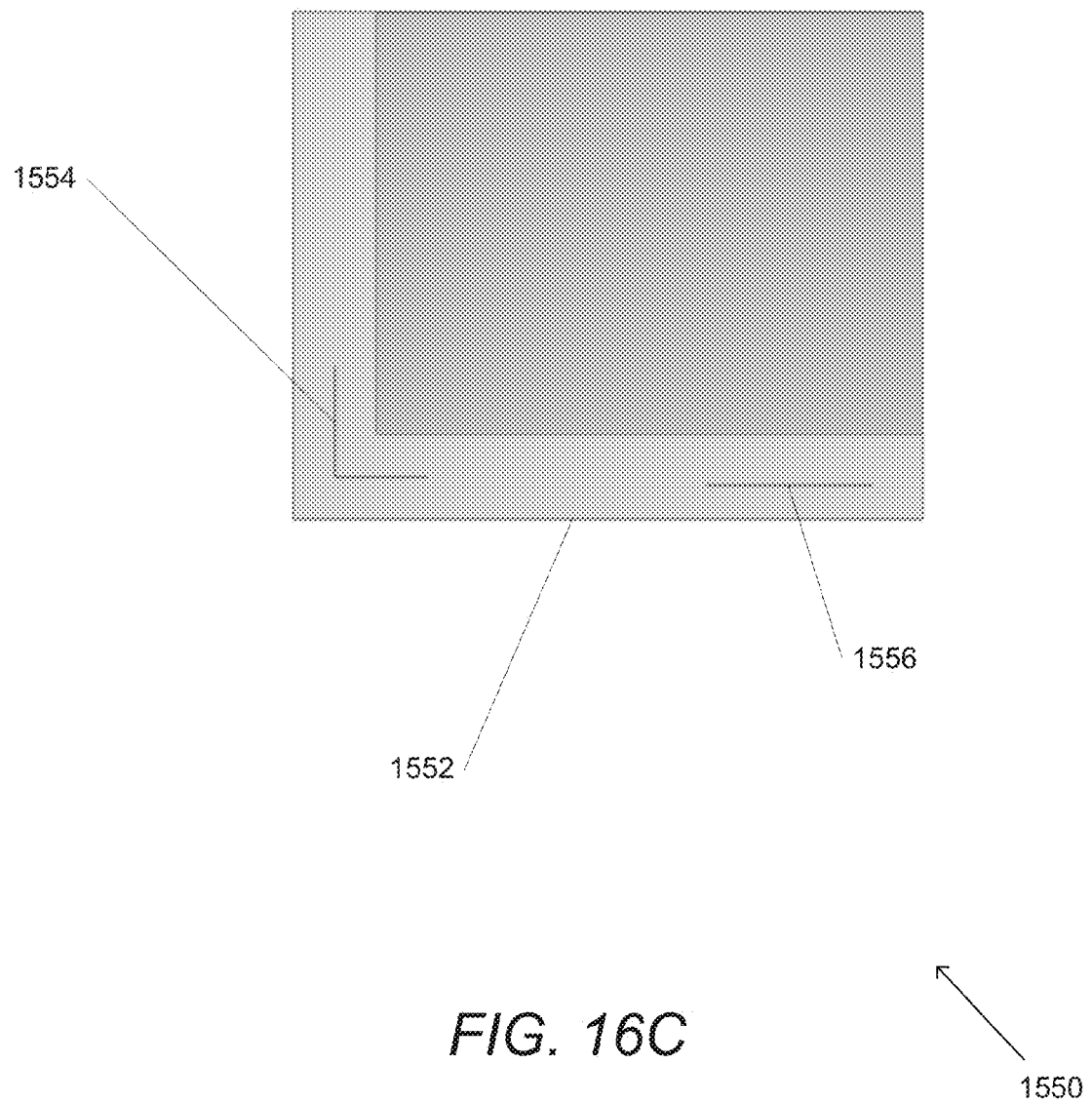

An embodiment using 8 antennas distributed around the periphery of an antenna unit in accordance with an embodiment of the invention is illustrated in FIGS. 16A-C. An embodiment using 8 patch radiator antennas in accordance with an embodiment of the invention is illustrated in FIG. 16A. The embodiment 1500 includes a plastic radome 1502 attached to the outer edge of an aluminum chassis 1504 (typically 10"×10"). In many embodiments, eight patch radiator antennas 1506 are contained inside the plastic randome 1502 and distributed around the periphery of the antenna unit. A schematic illustrating dimensions of an embodiment in accordance with an embodiment of the invention is illustrated in FIG. 16B. The embodiment 1530 includes an aluminum chassis 1534 that has a length of 10" and width of 4". On each side of the aluminum chassis 1534, a plastic randome 1532 of 1" by 4" is attached and a patch radiator antenna 1536 is contained within the plastic randome 1532. A portion of an embodiment using patch antennas in accordance with an embodiment of the invention is illustrated in FIG. 16C. The embodiment 1550 includes a plastic randome 1552 that has a patch radiator wrapped around a corner 1554 and a patch radiator located in the middle of a side 1556.

Various designs of the antenna units including precise dimensions and placement of patch radiator antennas can be implemented. In many embodiments, the "corner" beams are implemented by driving two patches on adjacent sides of the enclosure. In several embodiments, a patch that is wrapped around the corner of an antenna unit may be utilized. In a variety of embodiments, the number of antennas may be reduced and still resolve multiple targets.

As discussed above, FINDER systems can use separate antennas for transmitting and receiving. Using separate antennas also facilitates achieving sufficient isolation between transmit and receive paths, reducing the level of the cancellation signal required, which increases the system sensitivity for victim target returns. The separation of paths can allow the use of separate "probe" antennas for searching enclosed cavities and similar spaces.

In various embodiments, RF module transmit and receive signals are switched to the various antennas by means of monolithic RF switches. This allows not only looking in different directions (e.g. to identify targets behind the antenna unit which may show up as phantom reflections), but also the combining of antennas to create different shape or width beams. Further, the low RF power in the FINDER (typically less than 10 mW) allows the use of inexpensive monolithic switches with integrated drive electronics. In several embodiments, the antenna switching can also be used to select whether an external probe antenna is used. Further, in a variety of embodiments, dedicated multiple RF modules, each dedicated to an antenna can be utilized eliminating the need to perform antenna switching.

Although specific antennas and their configurations are discussed above with respect to FIG. 15-16C, any of a variety of antennas and configurations as appropriate to the requirements of a specific application can be utilized in accordance with embodiments of the invention. RF Modules for victim detection in accordance with embodiments of the invention are further discussed below.

RF Modules

Figure 17:
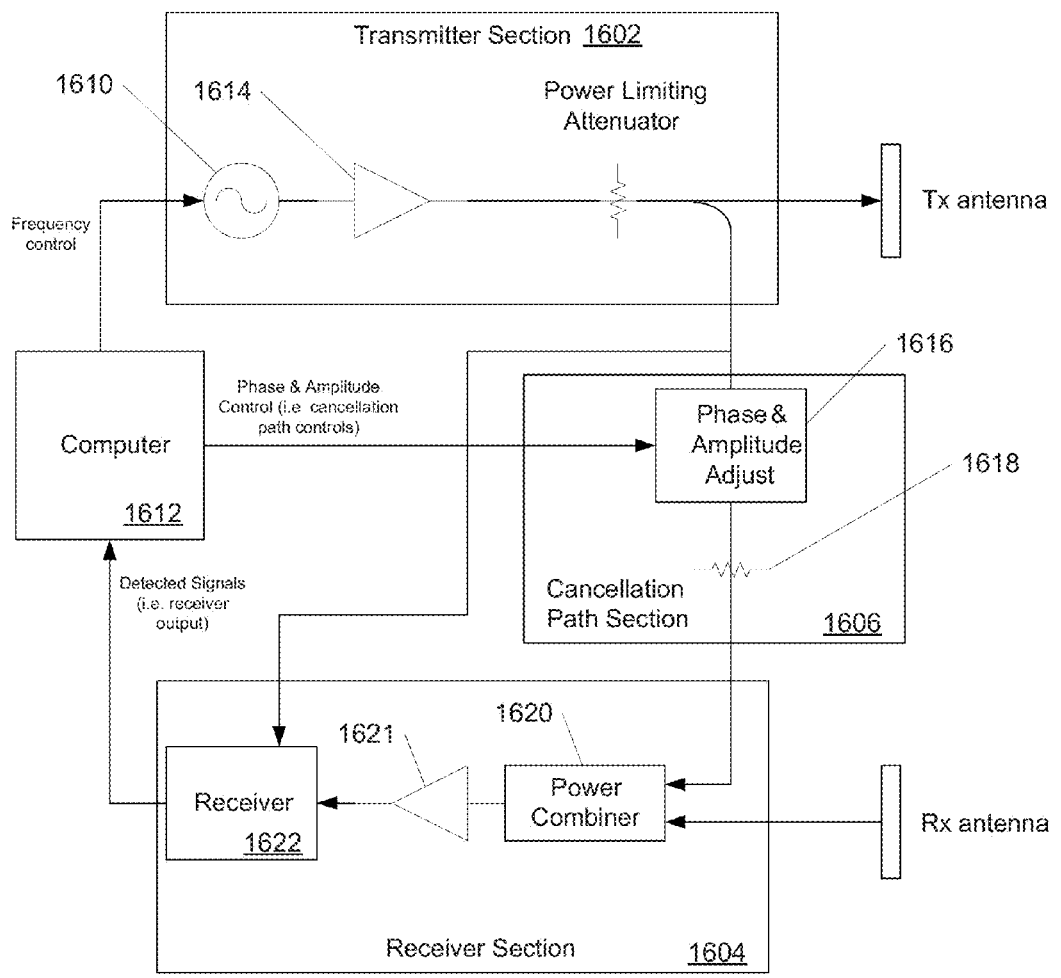
FIG. 17 is a block diagram illustrating an RF module in accordance with an embodiment of the invention.

The RF module can be a single channel and single beam CW FM radar. An RF module in accordance with an embodiment of the invention is illustrated in FIG. 17. The RF module 1600 can be divided into three sections: a transmitter section 1602 which generates the variable frequency signal radiated towards the rubble; a receiver section 1604 which demodulates the signals reflected from the rubble (and victim); and the cancellation path section 1606 which is used to cancel out the unchanging response (i.e. clutter), leaving just the changing signal (i.e. target reflection). The RF module can also include frequency controls, cancellation path controls (as two signals, I and Q), and receiver output (as two signals, I and Q). In many embodiments, the transmitter section includes a variable frequency microwave source where a Voltage Controlled Oscillator ("VCO") 1610 is driven by a Digital to Analog Converter (DAC) controlled by a computer 1612 to set frequencies for transmit signals. The VCO output is followed by filters and buffer amplifiers 1614 resulting in a 1-10 mW signal. The transmitter section can also include power dividers that take a coherent sample of the transmitted signal where the sample signal can be used for the cancellation signal and to set the local oscillator for the receiver's demodulator. In many embodiments, the cancellation path section can use an I/Q vector modulator 1616 to adjust the amplitude and phase 1616 of the cancellation signal. The I/Q inputs can be driven from DACs in the digital module, which are controlled by the computer to optimally cancel the fixed clutter signal. Any gain or offset imbalance in the I/Q inputs can be compensated by adjusting the DACs in a closed loop process. Since the control signals are essentially direct current ("DC") signals, any phase imbalance would manifest as something that can be controlled by the gain and offset. In several embodiments, the cancellation path includes a 20 dB attenuator 1618 to move the adjustment range closer to the expected level of the clutter signal. The value of the attenuator can be adjusted for optimum performance. In various embodiments, resistive voltage dividers can be used to scale the output of the DAC to appropriate levels for the vector modulator.

In several embodiments, the receiver section 1606 of the RF module can include a bandpass filter to select frequencies utilized by the radar and to remove the unwanted signals from adjacent bands. The demodulator is essentially a direct conversion to baseband, so out of band image responses are not a concern, however there can be about 50 dB of gain in the receiver before the demodulation and so filtering avoids amplifying any out of band signals. After the initial filtering, the received signal can be combined with the cancellation signal from the cancellation path using a power combiner 1620 (a simple resistive combiner or even a microstripline directional coupler can provide a lower cost option). In many embodiments, the FINDER design is self-calibrated for each frequency, so changes in match or gain on either the cancellation signal or received signal are essentially compensated by the closed loop cancellation process. Field and laboratory testing have shown that a Low Noise Amplifier (LNA) may not be needed before the combiner and could be problematic because of the very strong signal coupled from the transmit antenna. A transmit/receive isolation of −20 dB is typically expected, so a radiated +10 dBm signal would appear at the receiver input at −10 dBm. With such a strong signal, front end gain is not typically needed. In many embodiments, a small ceramic bandpass filter 1621 with a nominal range around 2.8 to 3.4 GHz can be used before sending the signal to the receiver 1622. Although extending below lowest transmit frequency of 3.1 GHz, the filter can reduce potentially troublesome interference in the 2.45 GHz ISM band, which is used for everything from microwave ovens to WiFi links.

After most of the static clutter contributions to the received signal are removed, the remaining signal can then be amplified via a chain of bandpass filters and monolithic amplifiers. The bandpass filters can be identical to the one used at the input, inserted between each amplifier to reduce the chance of oscillation at an out of band frequency. The monolithic amplifiers in many embodiments are typical of MMIC devices with a bandwidth of DC to 8 GHz. The interstage filters reduce the possibility of there being spurious oscillations resulting from unwanted signals coupling from output to input at just the wrong phase.

In many embodiments, a power divider sends the signal to an I/Q demodulator and to a test port. The test port can be used to measure the total power or view the signal spectrum on a spectrum analyzer. Such an RF power measurement monitor port might be useful in system self-calibration and in initial adjustment of the cancellation signal, particularly if the signal is strong enough to saturate the I/Q demodulator. However, any anomalies in the receive chain can be determined by looking at the output of the I/Q demodulator as the cancellation path is adjusted over the range of values. A 90 degree change in the cancellation path should show up as a comparable change in the output of the quadrature demodulator. As a result, several embodiments of the receiver module 1622 do not include a monitor port.

Typically, monolithic amplifiers are stable with almost any load. Further, at the low powers that are utilized, the power reflected from the antenna doesn't cause many problems with dissipation in the amplifier. Furthermore, leakage within the RF module from the transmit to receive side (e.g. Tx reflected power from the antenna mismatch coupling back through power dividers, etc.) is generally small, and essentially unchanging over time scales of minutes. In fact, the leakage looks like static returns from clutter, which can be cancelled by fundamental operations as discussed above.

Figure 18:
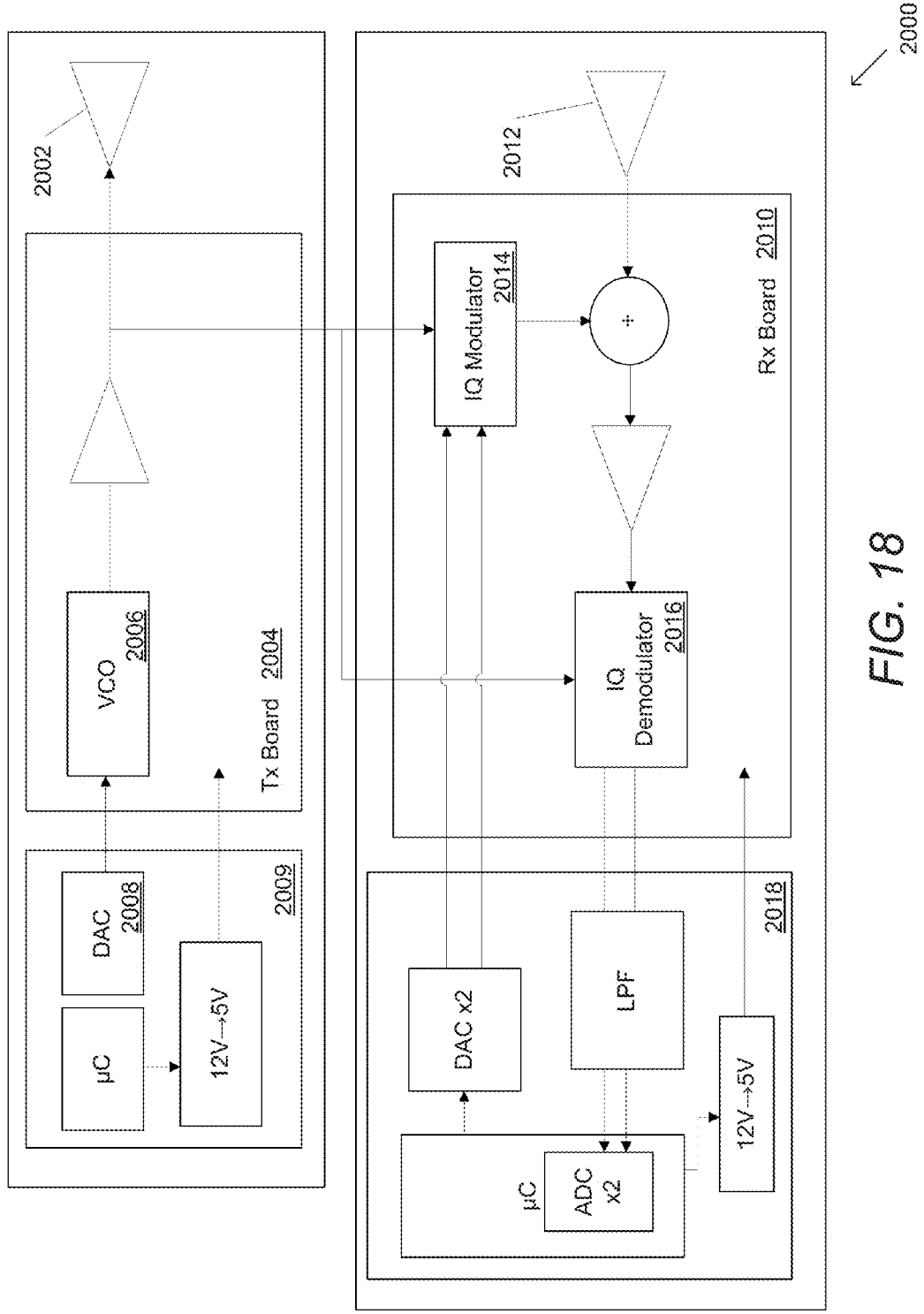
FIG. 18 is a block diagram illustrating separate transmit and receiver RF modules with digital interfaces in accordance with an embodiment of the invention.

Although a single RF module with a transmitter section and a receiver section are discussed above with respect to FIG. 17, an RF module can be separated into transmitter and receiver boards (i.e. transmit RF and receive RF modules) where each RF module is connected to a digital interface. An RF module in accordance with an embodiment of the invention is illustrated in FIG. 18. The RF module 2000 includes a transmit antenna 2002 that is connected to a transmitter board 2004. The transmitter board 2004 can include a VCO 2006 driven by a DAC 2008 that is part of the digital interface 2009. In various embodiments, the digital interface 2009 is connected to an embedded computer as described above. The RF module 2000 can also include a receiver board 2010 that is connected to a receive antenna 2012. The receiver board 2010 can include I/Q modulators 2014 and demodulators 2016 (and various buffers and amplifiers) for cancellation path processing as discussed above. In various embodiments, the receiver board 2010 is also connected to a digital interface 2018 that connects to an embedded computer for signal processing.

Figure 19:
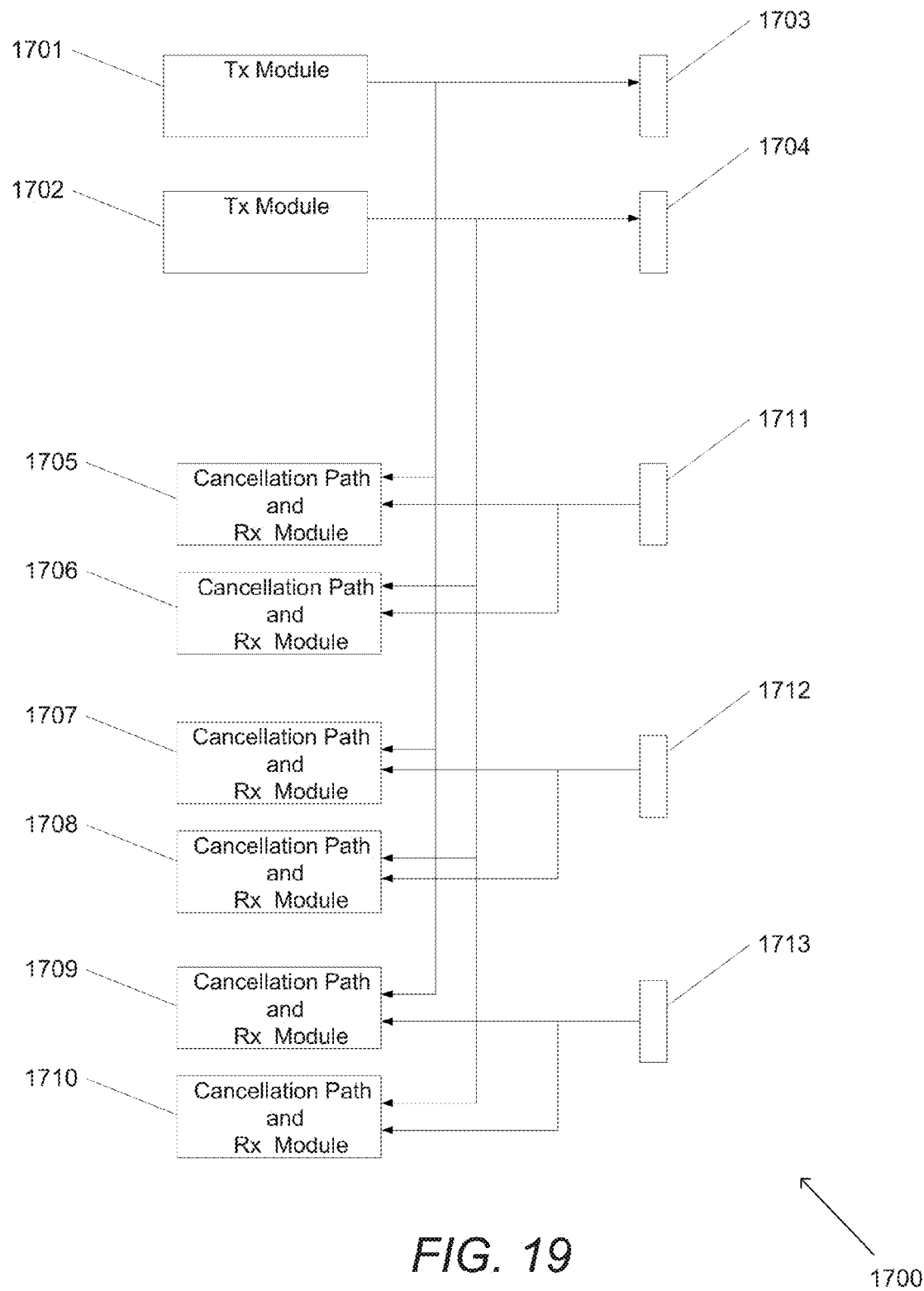
FIG. 19 illustrates an RF module with two transmitter and six cancellation path/receiver modules in accordance with an embodiment of the invention.

In a number of embodiments, a single board RF Module with a transmitter, cancellation path, and receiver all on one printed wiring board can be utilized. In several embodiments, the transmitter is on a separate board, allowing the use of a single transmitter with multiple receivers simultaneously. An RF Module with two transmitter and six cancellation path/receiver modules in accordance with an embodiment of the invention is illustrated in FIG. 19. The configuration 1700 includes two transmit modules 1701, 1702, two transmit antennas 1703, 1704, six receiver modules 1705-1710 (with cancellation paths), and three receive antennas 1711-1713 that can simultaneously process 6 beams and 2 frequencies.

In many embodiments, FINDER systems operate in the 3.1-3.4 GHz frequency bands as discussed above. FINDER systems will typically radiate no more than 10 mW from any antenna. This power level has been demonstrated to provide a sufficient signal to noise ratio to detect targets. Further, this relatively low level reduces the power consumption from the batteries, contributing to small size, lower weight, and lower cost. In addition, 10 mW is low enough that the RF fields at the surface of the antenna unit are well below the maximum levels called out in IEEE/ANSI C95.1-2009.

Although specific RF modules are discussed above with respect to FIGS. 17-19, any of a variety of RF modules as appropriate to the requirements of a specific application can be utilized in accordance with embodiments of the invention. Digital Modules for use in FINDER systems in accordance with embodiments of the invention are further discussed below.

Digital Modules

FINDER systems can include one or more digital modules that contain data converters (ADC and DAC) serving as the interface between RF modules and the signal processing software. Typically, a microcontroller or FPGA can read ADCs at a rate of 100-200 ksps. In many embodiments, sampled data can be filtered and decimated (reduction in sampling rate) to a few hundred samples/second for target detection. The digital module also provides a high level interface to the DACs that control the VCO frequency and the I/Q control voltages for the cancellation path.

Although an off the shelf data acquisition system can be used, the digital module can be implemented with monolithic integrated circuit ADCs similar to those used in digital audio systems. The ADC may be either integrated with the microcontroller or a separate device, depending on the overall system design. One factor in the trade is the number of beams and frequencies used to achieve the desired performance, which in turn affects whether multichannel data converters should be used.

In various embodiments, a testing unit can be an off the shelf National Instruments Compact RIO (cRIO) unit with ADC, DAC, and digital plugins. In various embodiments, this can be replaced by a single card with data converters and the necessary digital processing for filtering. The interface between the digital module and the embedded computer can includes a variety of data transfer standards including (but not limited to) Universal Serial Bus ("USB") or Ethernet. Typically, the ADC has sufficient conversion speed to allow sampling the output of the I/Q demodulator signals. There is a tradeoff with conversion speed—fast conversions relax the requirements on the low pass filters at the I/Q outputs, while consuming more power and introducing more digital noise. Slower conversions can involve lower cutoff frequencies on the low pass filter with the added advantage of lower power consumption. However, the lower cutoff frequency of the analog filters ahead of the ADC can increase the amount of time it takes for the values to stabilize. A fast conversion typical utilizes digital processing to filter and decimate to a reasonable rate for the heartbeat detection and victim detection processes.

The basic sample rate for victim detection can be 300-500 Hz, which is roughly 100 times faster than the heart rate which is about 0.5 to 2 Hz (usually given as 30-120 beats per minute). This sample rate is sufficiently high for adequate resolution of the fine structure and morphology of the heartbeat (and respiration) signals. In many embodiments, a decimated sample rate of 200 Hz can be selected. This rate is sufficiently higher than the heart and breathing, and their harmonics. As previously discussed, the FINDER typically operates between frequencies and/or beams and revisits the same beam/frequency combination at a 500 Hz rate. With 16-32 beam/frequency combinations, there is approximately 62.5 microseconds per beam/frequency implying that the ADC measurement can be made in around 50 microseconds. This allows for 10 microseconds for the microwave oscillator and cancellation paths to settle. Thus, analog filters on the I/Q output should have a time delay/settling time on the order of 10-20 microseconds, or around 50-100 kHz cutoff.

The I/Q control for the cancellation path can have more stringent requirements than the VCO tuning. The settling time can be chosen as one microsecond for the same reasons as the VCO tuning DAC. The DAC should have enough bits that it does not limit the accuracy with which the DC I/Q voltages are set, rather the performance should be limited by the modulator and other components. The modulator performance specification typically is called out as a Carrier Suppression/Nulling, and for the device selected for specific embodiments, it is −40 dB. This specification provides some guidance, but it is not directly usable since it defines the performance where I/Q are driven by sine waves with the DC offset adjusted to minimize the carrier signal. This performance implies that the DC bias can be set to 1 part in 100 (40 dB in power is a factor of 100 in voltage), or about 7-8 bits equivalent resolution. In FINDER applications where the I/Q inputs are DC voltages substantially better performance is typical. Laboratory measurements of specific modulators using a precision power supply have shown that 10 mV steps out of 60V (corresponding to about 0.3 mV out of a 2 V swing), or 1 part in 6000 can be easily resolved using a vector network analyzer to measure the phase and amplitude. This corresponds to around 13 bits of resolution. Therefore a DAC with 16 bit performance can be utilized. Typically, a perfect null is not required and with the gain distribution signals can be seen in less than ideal conditions.

The DAC should have enough bits to step in small enough frequency intervals to support some level of range processing using stepped frequency CW. In general, this suggests that the phase difference of the microwave signal at the maximum range should vary less than 180 degrees between two successive steps. For a maximum range of 30 meters, a round trip distance 60 meters, this is 5 MHz. For a typical monolithic VCO tuning voltage range of 0 to 5V tuning over the entire 300 MHz range, this means at least 60 steps or a 6 bit DAC should be chosen.

In many embodiments, the DAC should settle fast enough that FINDER can step between frequencies or beams and have enough time for the I/Q demodulator measurements to settle, before moving to the next combination. The VCO modulation bandwidth for typical VCOs is >50 MHz (implying response times of 20 ns or faster), so the DAC response and settling can be the limiting factor. In various embodiments, low pass filtering can be applied in the analog tuning voltage chain to avoid unwanted noise modulation, thus, a notional low pass of 100-200 kHz can be selected, and the DAC should convert in less than a microsecond.

Although specific digital modules are discussed above, any of a variety of digital modules as appropriate to the requirements of a specific application can be utilized in accordance with embodiments of the invention. Radar signal processing for target detection in accordance with embodiments of the invention are further discussed below.

Radar Signal Processing

Figure 20:
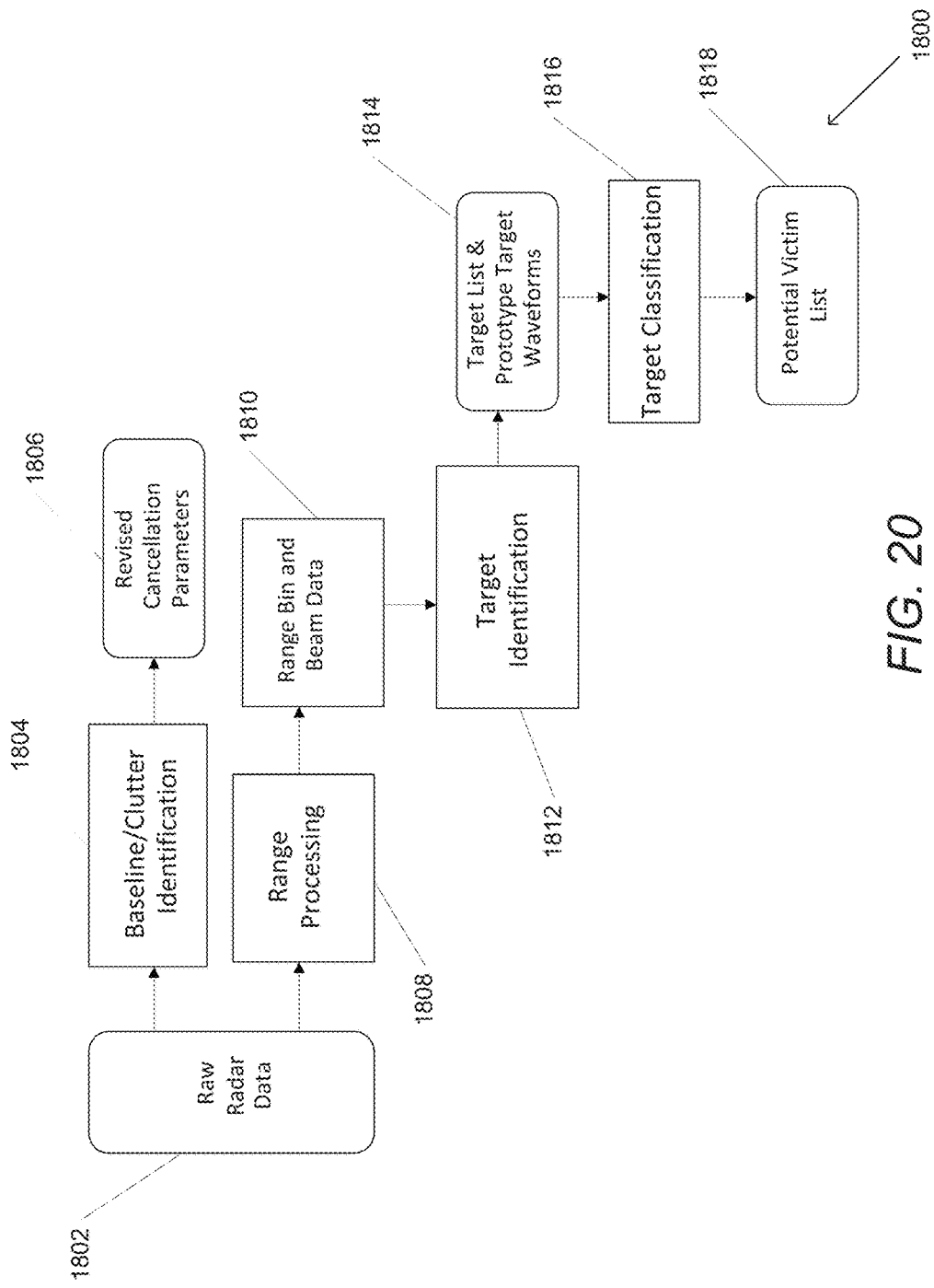
FIG. 20 illustrates a signal processing data flow diagram in accordance with an embodiment of the invention.

Radar signal processing can be performed for calibration and baseline/clutter removal, forming beams and range bins (if needed), identifying targets within those beams and range bins, and categorizing targets as human or other. A data flow chart of radar signal processing in accordance with an embodiment of the invention is illustrated in FIG. 20. The process 1800 starts with raw radar data (1802) from the receiver and includes performing (1804) baseline removal and clutter cancellation. In many embodiments, each time a search is performed, a one second recording is made from all beams and frequencies to determine the current static clutter characteristics. The optimum I/Q cancellation path values are calculated and/or revised (1806) using the previous value as a starting point. The new values are loaded to the hardware interface module and the process is repeated until the clutter is at an acceptably low level. If after some predetermined number of attempts, an adequate cancellation cannot be achieved, an error message is produced for the user indicating what frequencies and beams cannot be cancelled. If all beams have a problem at the same frequency, then it might indicate that FINDER is receiving interference from some other source. If a given beam cannot be cancelled, it may be that the antenna is obstructed or broken. In any case, the user has the option to continue with degraded operation.

The process 1800 also includes taking the raw radar data (1802) and performing (1808) range processing where the stepped frequency data is taken and an inverse Fast Fourier Transform (FFT) can be applied to turn the frequency domain data into an equivalent time domain profile. This can be a low resolution process, producing (1810) a dozen or so range bins, each one of which has a "slow time" sequence of I/Q samples at the 300-500 Hz sample rate which will be used for target identification. In many embodiments, the process 1800 includes target Identification attempts (1812) to find unique targets in one or more beam and range bins by examining a band limited version of the signal for repetitive characteristics within the typical heart rate. This can be done by a combination of autocorrelation and other methods which relies on the fact that while a given individual's heart rate may vary, the general shape of their MCG waveform does not (it merely stretches and shrinks). The output of the target identification process is a set of prototype waveforms (1814) which is essentially the normalized shape of a single heartbeat. There is one set of data for each potential victim and data which identifies which beams/ranges that signal appears in. Each target can also include data about the variability of that target.

In various embodiments, target classification can be performed (1816) and includes first identifying which targets are likely to be in the search area in front of the antenna unit, as opposed to on the side, for instance. Second, the algorithm compares the heart rate and respiration rate, and the morphology of the prototype waveform against a library of human and animal waveforms to distinguish between human, animal, and mechanical sources. For example, mechanical sources, e.g. a slowly rotating fan, tend to have very stable repetition rates that gradually decrease or increase. Human and animal sources actually vary somewhat from heartbeat to heartbeat with a classic 1/f flicker noise type power spectral density. Analysis of the heart data previously collected has shown that the width of the distribution is a simple statistic that has powerful separation properties. Upon target classification, a potential victim list can be generated (1818).

Although specific radar signal processing techniques for detecting victims are discussed above with respect to FIG. 20, any of a variety of radar signal processing techniques for detecting victims as appropriate to the requirements of a specific application can be utilized in accordance with embodiments of the invention.

While the above description contains many specific embodiments of the invention, these should not be construed as limitations on the scope of the invention, but rather as an example of one embodiment thereof. It is therefore to be understood that the present invention may be practiced otherwise than specifically described, without departing from the scope and spirit of the present invention. Thus, embodiments of the present invention should be considered in all respects as illustrative and not restrictive.

What is claimed is:

1. A life detecting radar comprising:
an antenna switching matrix configured to make multiple measurements at a same time comprising a plurality of transmit antennas configured to propagate a plurality of beams using continuous microwave signals stepping among a limited set of frequencies for obtaining range measurements, wherein switching and frequency patterns of the plurality of beams are selected to prevent the same frequency from being used on two separate beams at the same period in time;
at least one transmit antenna in the plurality of transmit antennas configured to propagate at least one beam using a continuous wave transmit signal set at a plurality of frequencies, where the at least one beam illuminates at least one sensing area;
at least one receive antenna configured to receive a return signal associated with reflections from objects of the at least one transmit signal within the at least one sensing area, where the return signal comprises at least one signal component having static phase associated with reflections from nonmoving objects and at least one signal component having time varying phase associated with at least one target;
a processor;
a memory containing a radar application, wherein execution of the radar application by the processor configures the processor to:
receive the return signal from the at least one receive antenna;
determine a static phase component of the return signal;
generate a cancellation signal at RF frequency by sampling at least one transmit signal and modulating the sampled transmit signal such that the phase and amplitude of the cancellation signal is adjusted to match an estimated phase and amplitude of the static phase component of the return signal;
process the return signal by subtracting the cancellation signal from the return signal to attenuate the at least one signal component having static phase; and
detect the at least one target by analyzing the at least one signal component having time varying phase for a biometric identifier by:
transforming the processed return signal from a frequency to a time domain data set;
generating range bins, where each range bin has a sequence of samples taken from the time domain data set;
analyzing each range bin for unique targets by examining a band limited version of the processed return signal for repetitive characteristics; and
matching the repetitive characteristics to a biometric identifier of a human, wherein the biometric identifier includes at least one microwave cardiogram (MCG) and at least one breathing pattern that can be utilized to discriminate among a plurality of unique targets located within the at least one sensing area, and wherein uniqueness of MCG allows for the separation of combined MCGs from multiple targets to discriminate among the targets.

2. The life detecting radar of claim 1, wherein the radar application further configures the processor to generate a user interface that allows the processor to receive inputs for controlling the life detecting radar.

3. The life detecting radar of claim 2, wherein the user interface is generated on a separate device configured to communicate with the life detecting radar via a wireless communication channel.

4. The life detecting radar of claim 1, wherein the plurality of transmit antennas are configured to rapidly switch the plurality of beams and frequencies to allow for multiple measurements to be made during a short enough time period wherein the at least one target's heartbeat signal is assumed constant during the time period.

5. The life detecting radar of claim 1, wherein the plurality of transmit antennas are configured to rapidly switch the plurality of beams and frequencies to allow for multiple measurements to be made during a short enough time period wherein the at least one target's respiration signal is relatively constant.

6. The life detecting radar of claim 1, wherein the radar application further configures the processor to receive the return signal from the at least one receive antenna and collect samples for each sensing area at a sampling rate between 300-500 Hz.

7. The life detecting radar of claim 1, wherein the life detecting radar utilizes a plurality of radio frequency modules that transmit and receive signals.

8. The life detecting radar of claim 1, wherein the life detecting radar further comprises a camera for collecting digital image data.

9. The life detecting radar of claim 1, wherein the life detecting radar further comprises a Global Positioning System for providing location information.

10. The life detecting radar of claim 1, wherein transforming the processed return signal from a frequency to a time domain data set includes utilizing an Inverse Fast Fourier Transform.

11. The life detecting radar of claim 1, wherein the radar application further configures the processor to produce a prototype waveform from the at least one signal component having time varying phase and compare the prototype waveform against a data collection of human and animal waveforms to detect the at least one target.

12. The life detecting radar of claim 1, wherein detecting a target by analyzing the at least one signal component further includes first identifying which targets are likely to be in a search area in front of the transmit antenna.

13. The life detecting radar of claim 1, wherein the at least one transmit antenna is further configured to propagate eight beams arranged in cardinal and intermediate directions.

14. The life detecting radar of claim 13, wherein the at least one transmit antenna is further configured to utilize 10 frequencies.

15. The life detecting radar of claim 1, wherein the sequence of samples taken from the time domain data set includes phase and quadrature data samples.

16. The life detecting radar of claim 1, wherein at least one antenna is configured to be used as both a transmit antenna and a receive antenna.

17. The life detecting radar of claim 1, wherein the at least one transmit signal used to generate the cancellation signal is received by one of the at least one receive antennas.

18. A method of detecting a target using a processor of a life detecting radar, the method comprising:
propagating, using an antenna switching matrix comprising a plurality of antennas to make multiple measurements at a same time, a plurality of beams using continuous microwave signals stepping among a limited set of frequencies for obtaining range measurements, wherein at least one beam is propogated using a continuous wave transmit signal set at a plurality of frequencies, where the plurality of beams illuminate at least one sensing area using a plurality of transmit antennas and wherein switching and frequency patterns are selected to prevent the same frequency from being used on two separate beams at the same period in time;

receiving a return signal associated with reflections of the at least one transmit signal from objects within the at least one sensing area using at least one receive antenna, where the return signal comprises at least one signal component having static phase associated with reflections from nonmoving objects and at least one signal component having time varying phase associated with at least one target;

receiving the return signal from the at least one receive antenna using a life detecting radar system;

determining a static phase component of the return using the life detecting radar system;

generating a cancellation signal at RF frequency by sampling the at least one transmit signal and modulating the sampled transmit signal such that the phase and amplitude of the cancellation signal is adjusted to match an estimated phase and amplitude of the static phase component of the return signal using the life detecting radar system;

processing the return signal by subtracting the cancellation signal from the return signal to attenuate the at least one signal component having static phase using the life detecting radar system; and detecting the at least one target by analyzing the at least one signal component having time varying phase for a biometric identifier by using the life detecting radar system by:
  transforming the processed return signal from a frequency to a time domain data set;
  generating range bins, where each range bin has a sequence of samples taken from the time domain data set;
  analyzing each range bin for unique targets by examining a band limited version of the processed return signal for repetitive characteristics; and
  matching the repetitive characteristics to a biometric identifier of a human, wherein the biometric identifier includes at least one microwave cardiogram and at least one breathing pattern that can be utilized to discriminate among a plurality of unique targets located within the at least one sensing area, and wherein uniqueness of MCG allows for the separation of combined MCGs from multiple targets to discriminate among the targets.

19. A life detecting radar comprising:
an antenna switching matrix configured to make multiple measurements at the same time comprising a plurality of transmit antennas configured to propagate a plurality of beams using continuous microwave signals stepping among a limited set of frequencies for obtaining range measurements wherein switching and frequency patterns are selected to prevent the same frequency from being used on two separate beams at the same period in time;

at least one transmit antenna in the plurality of transmit antennas configured to propagate eight beams using continuous wave transmit signals set using ten frequencies, where:
  the eight beams are arranged in cardinal and intermediate directions and illuminate a plurality of sensing areas to resolve a twenty meter search range; and
  wherein the at least one transmit antenna is configured to rapidly switch among the eight beams and ten frequencies to allow for multiple measurements to be made during a short enough time period wherein a target's biometric identifiers are relatively constant;
at least one receive antenna configured to receive a return signal associated with reflections from objects within the at least one sensing area of the at least one transmit signal, where the return signal comprises at least one signal component having static phase associated with reflections from nonmoving objects and at least one signal component having time varying phase associated with at least one target;
a processor;
a memory containing a radar application, wherein execution of the radar application by the processor configures the processor to:
  receive the return signal from the at least one receive antenna and collect samples for each sensing area at a sampling rate between 300-500 Hz;
  determine a static phase component of the return signal;
  generate a cancellation signal at RF frequency by sampling the at least one transmit signal and modulating the sampled signal such that the phase and amplitude of the cancellation signal is adjusted to match an estimated phase and amplitude of the static phase component of the return signal, where the at least one transmit signal used to generate the cancellation signal is received by one of the at least on receive antennas;
  process the return signal by subtracting the cancellation signal from the return signal to attenuate the at least one signal component having static phase; and
  detect the at least one target by analyzing the at least one signal component having time varying phase for a biometric identifier by:
    transforming the processed return signal from a frequency to a time domain data set;
    generating range bins, where each range bin has a sequence of samples taken from the time domain data set;
    analyzing each range bin for unique targets by examining a band limited version of the processed return signal for repetitive characteristics; and
    matching the repetitive characteristics to a biometric identifier of a human, wherein the biometric identifier includes at least one microwave cardiogram and at least one breathing pattern that can be utilized to discriminate among a plurality of unique targets located within the at least one sensing area, and wherein uniqueness of MCG allows for the separation of combined MCGs from multiple targets to discriminate among the targets.

* * * * *